(12) United States Patent
Costi et al.

(10) Patent No.: US 8,916,679 B2
(45) Date of Patent: Dec. 23, 2014

(54) PEPTIDES BINDING TO THE DIMER INTERFACE OF THYMIDYLATE SYNTHASE FOR THE TREATMENT OF CANCER

(75) Inventors: Maria Paola Costi, Modena (IT); Gaetano Marverti, Arceto (IT); Daniela Cardinale, Modena (IT); Alberto Venturelli, Maranello (IT); Stefania Ferrari, Pavullo Nel Frignano (IT); Glauco Ponterini, Modena (IT); Stefan Henrich, Heidelberg (DE); Outi Salo-Ahen, Turku (FI); Rebecca Wade, Heidelberg (DE)

(73) Assignees: Universita' degli Studi di Modena e Reggio Emilia, Modena (IT); Heidelberg Institute For Theoretical Studies (Hits), Heidelberg (DE)

( * ) Notice: Subject to any disclaimer, the term of this patent is extended or adjusted under 35 U.S.C. 154(b) by 0 days.

(21) Appl. No.: 13/513,480

(22) PCT Filed: Dec. 1, 2009

(86) PCT No.: PCT/IB2009/055439
§ 371 (c)(1),
(2), (4) Date: Aug. 17, 2012

(87) PCT Pub. No.: WO2011/067624
PCT Pub. Date: Jun. 9, 2011

(65) Prior Publication Data
US 2012/0302511 A1 Nov. 29, 2012

(51) Int. Cl.
A61K 38/02 (2006.01)
A61K 38/03 (2006.01)
A61K 38/04 (2006.01)
A61K 38/05 (2006.01)
C07K 5/083 (2006.01)
C12N 9/10 (2006.01)
C07K 7/06 (2006.01)
C07K 5/093 (2006.01)
A61K 38/00 (2006.01)

(52) U.S. Cl.
CPC ............ *C12N 9/1007* (2013.01); *C07K 5/0808* (2013.01); *A61K 38/00* (2013.01); *C07K 7/06* (2013.01); *C07K 5/0819* (2013.01)
USPC ........................................... 530/300; 514/1.1

(58) Field of Classification Search
None
See application file for complete search history.

(56) References Cited

FOREIGN PATENT DOCUMENTS

| WO | 0239947 A2 | 5/2002 | | |
|----|----|----|----|----|
| WO | WO02072753 A1 * | 9/2002 | ............ | A61K 38/16 |
| WO | 2004081206 A2 | 9/2004 | | |
| WO | 2006124684 A2 | 11/2006 | | |
| WO | WO2008021290 A1 * | 2/2008 | ............ | G01N 33/53 |

OTHER PUBLICATIONS

"Collateral sensitivity to novel thymidylate synthase inhibitors correlates with folate cycle enzymes impairment in cisplatin-resistant human ovarian cancer cells". European Journal of Pharmacology, vol. 615, No. 1-3, Aug. 2009, pp. 17-26.
"A rationale for the clinical development of the thymidylate synthase inhibitor ZD9331 in ovarian and other solid tumours". Biochimica et Biophysica Acta, Jul. 18, 2002, vol. 1587, No. 2-3, pp. 215-223.
"Synthetic interface peptides as inactivators of multimeric enzymes: inhibitory and conformational properties of three fragments from *Lactobacillus casei* thymidylate synthase". Biochemistry, May 12, 1998, vol. 37, No. 19, pp. 6883-6893.
"Variants of human thymidylate synthase with loop 181-197 stabilized in the inactive conformation". Protein Science, vol. 18, No. 8 Aug. 2009. vol. 37, No. 19, pp. 1632-1634.
Written Opinion and Search Report dated Apr. 6, 2010.

* cited by examiner

*Primary Examiner* — Karlheinz R Skowronek
*Assistant Examiner* — Joseph Fischer
(74) *Attorney, Agent, or Firm* — Vorys, Sater, Seymour and Pease LLP; Susanne M. Hopkins

(57) ABSTRACT

Provided are peptides that bind to the thymidylate synthase protein, in particular to human thymidylate synthase (hTS) protein, for the treatment of cancer. Further provided are peptides that can bind at a binding site located at the interface of thymidylate synthase protein. These peptides range from 3 to 10, preferably 4-8 amino acids and have a sequence that binds to each subunit of the thymidylate synthase dimer at the level of dimer interface, stabilizing the dimeric inactive form of the thymidylate synthase enzyme. In addition, provided are pharmaceutical compositions including these compounds as active agents, and uses thereof for the treatment of cancer and to reverse or/and be active in cancer drug resistance.

22 Claims, 8 Drawing Sheets

```
           12          22          32          42          52          62
MRGSHHHHHHGS MPVAGSELPR RPLPPAAQER DAEPRPPHGE LQYLGQIQHI LRCGVRKDDR
 72          82          92         102         112         122
TGTGTLSVFG MQARYSLRDE FPLLTTKRVF WKGVLEELLW FIKGSTNAKE LSSKGVKIWD
132         142         152         162         172         182
ANGSRDFLDS LGFSTREEGD LGPVYGFQWR HFGAEYRDME SDYSGQGVDQ LQRVIDTIKT
192         202         212         222         232         242
NPDDRRIIMC AWNPRDLPLM ALPPCHALCQ FYVVNSELSC QLYQRSGDMG LGVPFNIASY
252         262         272         282         292         302
ALLTYMIAHI TGLKPGDFIH TLGDAHIYLN HIEPLKIQLQ REPRPFPKLR ILRKVEKIDD
312         322         325
FKAEDFQIEG YNPHPTIKME MAV
```

Fig. 1

PEPTIDES BINDING TO THE DIMER INTERFACE OF THYMIDYLATE SYNTHASE FOR THE TREATMENT OF CANCER

This is a National Phase Application filed under 35 U.S.C. §371 as a national stage of PCT/IB2009/055439, filed on Dec. 1, 2009, the content of which is hereby incorporated by reference in its entirety.

The present invention relates to peptides binding to the thymidylate synthase protein, in particular to human thymidylate synthase (hTS) protein, for the treatment of cancer.

Cancer is a disorder in which a population of cells has become, in varying degrees, unresponsive to the control mechanisms that normally modulate proliferation-differentiation balance. Cancer cells display uncontrolled growth (growth and division beyond the normal limits), invasion (intrusion on and destruction of adjacent tissues), and sometimes metastasis (spread to other locations in the body via lymph or blood).

The Sequence Listing submitted in text format (.txt) on Jun. 1, 2012, named "seql.txt", (created on Thursday, May 31, 2012, 34.3 KB), is incorporated herein by reference.

Therapeutic agents used in clinical cancer therapy can be categorized into several groups, including, alkylating agents, antibiotic agents, antimetabolic agents, biologic agents, hormonal agents, and plant-derived agents. The explosion of knowledge regarding the biology of cancer has led to the identification of several new molecular targets for drug development both to meet the increasing therapeutic requirements and to overcome drug resistance. Nevertheless, several difficulties hinder satisfactory headway.

In particular, therapeutic treatment outcomes rely on the type of cancer and the genetic predisposition of the patient. Moreover, the narrow therapeutic index of cytotoxic drugs and the appearance of drug resistance mean recurrence of disease or unfavorable prognosis for patients. Several cancers, like ovarian cancer for example, are life-threatening pathologies because of the rapid development of drug resistance, in particular to platinum derived drugs, which constitute the largest class of anti-cancer drugs in the clinic and the most important one in terms of treatment.

An alternative and particularly interesting approach to cancer therapy is controlling the enzymatic activity of target proteins in malignant cells. The inhibition of the enzymes involved in the formation of purine and pyrimidine nucleotide precursors, for example, causes DNA-RNA synthesis impairment and consequently, cell growth is compromised, in particular rapidly dividing cancer cells are affected. However, this therapeutic approach is hampered by: 1) the cross resistance of platinum drugs and 2) the resistance mechanism that arises owing to down-modulation of the expression of several of the enzymes involved in the possible metabolic routes of nucleotides/folates metabolism. For these reasons, novel candidates with a new mechanism of action against this pathway can be of success in reversing drug resistance and providing new therapeutic approaches.

As said before, nucleotide metabolism depends on several pathways and consequently, inhibition of some enzymes can be circumvented by one or more alternative routes. A noteworthy exception is the Thymidylate synthase (TS) enzyme, a "bottleneck" enzyme that provides the only way of adding a methyl group to the 5-position of the pyrimidine ring in the de novo synthesis of thymidine. Since thymidine is the only nucleotide precursor specific to DNA, TS is an excellent target for anticancer drugs but, to achieve thymidylate deprivation leading to growth arrest and cell death, the levels of TS catalytic activity must be reduced significantly.

In the Thymidylate synthesis cycle (see FIG. 2), dietary folate is reduced to dihydrofolate, which is further reduced by the enzyme dihydrofolate reductase to tetrahydrofolate, using the reduced form of nicotinamide adenine dinucleotide phosphate as a hydrogen source. Tetrahydrofolate is then converted to methylenetetrahydrofolate by the enzyme serine transhydroxymethylase, which uses vitamin B6 as a cofactor. The methylene-group-carrying cofactor, methylenetetrahydrofolate, then provides both a methylene group and reducing activity, to convert dUMP to dTMP by the action of the thymidylate synthase enzyme. Thymidylate synthase activity is a two-stage process, firstly involving, as just discussed, deoxyuridine monophosphate (dUMP) binding to a receptor site; this favours the binding of N-5,10-methylene-tetrahydrofolate. The second step involves transferring the folate's one carbon group to the uridine ring, yielding deoxythymidine monophosphate (dTMP) and dihydrofolate. dTMP is subsequently phosphorylated by a kinase to dTDP and dTTP, one of the bases for DNA synthesis (see FIG. 2).

The human Thymidylate synthase enzyme is a dimer of two identical subunits. The dimeric protein is characterized by a molecular weight ranging from 60 to 75 kDa depending on the organism source and is very stable and shows a dissociation constant ($K_d$) of 100 nM. The interface is highly conserved and almost 50% of the interface residues are invariant/almost invariant. Within the cell environment the human TS concentration varies in the range of 50-200 nM during the cell cycle. Several reports show that TS protein also binds to its mRNA and to a number of mRNAs in vitro, including c-myc, bcl-2 and p53. The biological meaning of these ribonucleoproteic complexes remains mainly unknown, but it suggests that in addition to its role as a catalytic protein, it participates in the regulation of synthesis of other proteins involved in cell cycle, DNA repair and transcription. Recently it has been reported that increased levels of TS transcriptional factor E2F-1 improve TS expression and consequently contribute to the activation of oncogenic factors acting indirectly as tumor inducers. These data demonstrate that increased levels of TS are not only responsible for drug resistance, but as a major drawback, counteract the efficacy of the enzymes, thus favoring the progress of the malignancies.

E. Chu and co-workers (*Nucleic Acid Research*, 1996, Vol. 24, No. 16 p. 3222-8) have studied in detail the TS pathway related to the feedback regulation of TS expression. In the proposed model, the TS protein in its unbound form interacts with TSmRNA and mRNA sequences encoding for several proteins, thus acting as a translational inhibitor. This model explains an important resistance mechanism developed towards TS inhibitors used in anticancer chemotherapy, because it is evident that the inhibitor bound complex induces an over expression of the TS protein as a late response, thus lowering the efficacy of the drug. Moreover, the dimer-monomer equilibrium of all the different TS isoforms and the related proteic conformational changes play a key role in the catalysis. Indeed, they allow the correct alignment of the reactants, contribute to catalysis by positioning a general acid near the methyl transfer site, and force bound substrates into strained conformations, which activate atoms on the substrate or co-factor.

A recent study by Berger S. H. et al. (*Biochimica et Biophysica Acta*, 2004, Vol 1696, 15-22) highlights the presence of different human TS conformational states, pre-existing with respect to the catalytic reaction (see FIG. 3). In the "active" conformation, the catalytic Cys-195 is positioned in the active site while, in the "inactive" conformation, it is at the subunit interface. In particular, the inactive dimeric form (AAi) is in equilibrium with the active unbound form (AAa) and a ternary complex (AAL, L is for ligand), which is the bound form. The active conformation of human TS binds substrates and carries out its catalytic function. Structurally, active human TS shows the catalytic Cys-195 positioned in the active site and has region 107-128 (small domain) folded, while inactive conformation of human TS binds four phosphate ions, is not a catalyst and its 107-128 region (small domain) is unfolded and disordered in crystals.

Moreover, the active conformation exists in an open form, as shown by the X-ray crystal structures obtained so far. The inactive dimeric form is unstable towards degradation, while the ternary complex is more stable to degradation, and this property prolongs the life of the protein and its regulatory function modulating TS intracellular concentration. The native protein exists in apparent equilibrium between the two conformational states, while TS-inhibitor-bound enzyme assumes the active conformation. The native protein has been reported to bind its own mRNA and several other mRNAs, but the bound structure loses its RNA binding activity and stabilizes TS to turnover. In particular, through a translational auto regulation mechanism involving TS protein binding to its own mRNA on two distinct regions, TS protein controls its own cellular expression level.

Deeper knowledge of the TS biology has suggested the existence of a monomeric form of TS in equilibrium with its dimeric form. Binding studies on the interaction of peptides taken from the complete sequence of *Homo sapiens* TS (hTS) with the TSmRNA sequence suggested that the protein domain for binding to the regulatory sequences on TSmRNA is located at the interface of the two monomers. A complex equilibrium is present at the intracellular level and each molecular form shows different functions. Some studies have been made on the process of unfolding/refolding of the obligate homodimer TS of *Lactobacillus casei* (LcTS). Three synthetic peptides corresponding to the interface regions of LcTS were identified and tested for their ability to function as inhibitors by modifying the quaternary structure of the enzyme.

Allegra C. and co-workers (*Biochemical and Biophysical Research Communications*, 297, 2002, 24-31 and relative WO02/072753) have recently suggested the existence of a monomeric form of TS in equilibrium with its dimeric form and this balance defines cell sensitivity to TS inhibitors.

Using a separate series of overlapping 17-mer peptides spanning the length of both the human and *Escherichia coli* TS sequences, six potential domains located in the homodimeric interface region of the TS protein that bind TSmRNA have been identified. Studies on the interaction of these peptides with the TSmRNA sequence have demonstrated that the hTS domain involved in the binding to regulatory sequences on TSmRNA is located at the monomer interfaces of the hTS dimeric form. The access of macromolecules like RNA to the interface region between two monomeric subunits is limited, suggesting that the protein interacts with its own mRNA when it is in a monomeric form. Indeed a monomeric form of TS protein exists in solution despite the well-established fact that the enzyme is an obligate dimer for its catalytic function.

Summarising the results of Berger and Allegra, it seems that a monomeric inactive conformation responsible for binding mRNA should exist. However, further studies are needed in order to describe the first equilibrium drawn in FIG. 3 in detail: it is not clear whether the monomeric form seen by Allegra and co-workers is active or inactive or whether the dimeric inactive form seen by Berger and co-workers is formed by the inactivation of the dimeric active form or by the dimerisation of two inactive monomers.

However, the data presented by Allegra and Berger explain in part the mechanism of action of several TS inhibitors currently used in chemotherapy that are exclusively substrate analogues that compete with the substrate, bind to the active site and stabilize human TS active conformations forming the human TS dimeric active bound conformation (AAL). This binding inhibits the enzyme and slows down its degradation. Nevertheless, it is known that TS (dimeric) active (bound) conformation cannot bind mRNA and, consequently, using an excess of TS substrate or inhibitors leads to repression of protein binding to mRNA, resulting in increased translational efficiency and ultimately drug resistance due to increased levels of TS protein.

These observations clearly mean that the classical active site inhibition cannot cause a prolonged and sufficiently persistent down-regulation of the DNA synthesis pathway and therefore alternative approaches of inhibition of this protein are needed to produce the effect of down-regulating the cancer cells and driving them towards cell death.

The technical problem faced by the present invention is that of providing inhibitors of Thymidylate synthase (TS) protein, in particular human TS protein for use in the treatment of cancer as alternatives to existing anticancer drugs.

Another problem faced by the present invention is that of providing anticancer drugs able to reverse cancer resistance to known anticancer medicaments.

The above problems have been solved by the authors of the present invention that have found that small peptides binding to the TS dimer interface are able to inhibit TS, through a "non-canonical" way. The authors have found that said peptides are able to treat cancer and to reverse cancer resistance to known anticancer medicaments, either when administered alone or in combination with known anticancer drugs.

The following description of the invention is done with reference to the attached figures in which:

FIG. 1 shows the amino-acid sequence of the histidine-tagged human thymidylate synthase (ht-hTS); the 12-residue histidine tag added at the N-terminus of the hTS sequence is indicated in gray; the residues involved in the peptide binding and the catalytic Cys residues are underlined; the sequence of the construct is shifted by 12 units with respect to that of the holoenzyme (TS); the sequence numbering reported in the present application refers to the sequence of FIG. 1, where residue #1 is the Met starting the sequence MRGSHHH;

The present invention relates to peptides comprising or consisting essentially of from 3 to 10 amino acids, preferably from 4 to 8 amino acids, able to bind at a site located at the Thymidylate synthase (TS) dimer interface.

The peptides inhibit TS through a new mechanism of action involving peptides binding to a newly identified TS binding site, located in the dimer interface region, and thereby stabilizing the TS inactive conformation. This newly identified binding property provides a tool to inhibit TS enzyme, retaining the TS translational repression function, in particular on its own mRNA, and avoiding cancer drug resistance due to high TS expression following classical TS inhibitor treatments in cancer.

Figure 6:
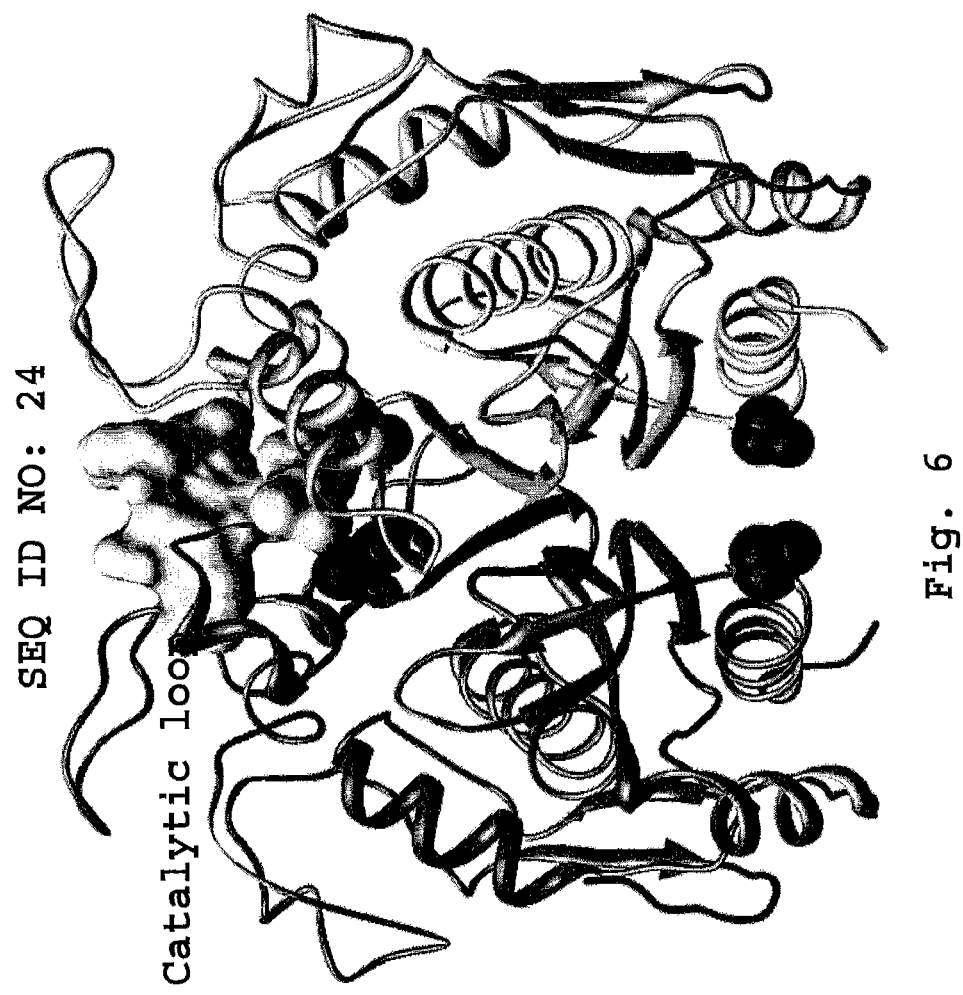
FIG. 6 shows the X-ray complex of the peptide corresponding to SEQ ID NO: 24 bound to human TS.

The inventors have demonstrated that the peptides bind at a previously unidentified site that is located at the interface between the two TS monomers, stabilising the inactive form of TS, through crystal structure determination of a complex between TS and a peptide (see FIG. 6). This X-ray crystal structure clearly shows that the peptide binds in an allosteric site thus reducing the TS activity, without large changes in the conformation of TS.

Accordingly, the peptides of the invention are useful in the treatment of cancers in which TS protein plays a central role. They can also be employed to reverse cancer resistance to known chemotherapeutic agents.

As used herein, the wording "Thymidylate synthase protein/enzyme (TS)" refers to human Thymidylate synthase (hTS). The sequence of histidine-tagged human thymidylate synthase (ht-hTS) is reported in FIG. 1 and in the sequence listing as SEQ ID NO: 186.

The binding site of the peptide, as found in the crystal structure of hTS, spans the cleft located at the interface of the two hTS subunits defined by loops 149-172 and 183-204 of both A and B subunits. The cleft comprises Cys192 and is close to the catalytic Cys207 (the loops and the Cys residues are underlined in FIG. 1).

The peptides can be administered either alone or in conjunction with known anticancer drugs.

The peptides of the present invention can also be useful to treat, or reverse resistance to common anticancer drug of malignancies chosen in the group consisting of: solid tumor, hematological malignancy, carcinoma, neuroblastoma and melanoma.

A solid tumor is preferably a tumor of the head, neck, lung, breast, colon, prostate, bladder, rectum, brain, gastric tissue, bone, ovary, thyroid or endometrium.

Preferably, a hematological malignancy is leukemia, lymphoma or myeloma.

Preferred embodiments of a carcinoma include bladder carcinoma, renal carcinoma, breast carcinoma or colorectal carcinoma.

Further examples of malignancies that can be treated with the peptides of the invention include that of the head, neck, bladder, breast, colon, kidney, liver, lung, ovary, pancreas, stomach, cervix, thyroid and skin, including squamous and basal cell carcinoma, and other dermal malignancies; hematopoietic tumors of lymphoid lineage, including leukemia, acute lymphocytic leukemia, acute lymphoblastic leukemia, B-cell lymphoma, T-cell lymphoma, Hodgkins lymphoma non-Hodgkins lymphoma, hairy cell lymphoma, Burketts lymphoma and multiple myeloma; tumors of mesenchymal origin, including fibrosarcoma, rhabdomyosarcoma, and osteosarcoma; other tumors including melanoma, seminoma, teratocarcinoma, neuroblastoma and glioma; tumors of the central and peripheral nervous system, including astrocytoma, neuroblastoma, and schwannomas; and other tumors, including, xeroderma pigmentosum, keratoacanthoma, seminoma, thyroid follicular cancer and teratocarcinoma.

Other examples of cancers that can be treated with the compounds of the invention are selected from the group consisting of: diffuse large B-cell lymphoma (DLBCL), T-cell lymphomas or leukemias, (e.g. cutaneous T-cell lymphoma (CTCL), noncutaneous peripheral T-cell lymphoma, lymphoma associated with human T-cell lymphotrophic virus (HTLV), adult T-cell leukemia/lymphoma (ATLL)) as well as acute lymphocytic leukemia, acute nonlymphocytic leukemia, acute myeloid leukemia, chronic lymphocytic leukemia, chronic myelogenous leukemia, Hodgkin's disease, non-Hodgkin's lymphoma, myeloma, multiple myeloma, mesothelioma, childhood solid tumors, brain neuroblastoma, retinoblastoma, glioma, Wilms' tumor, bone cancer and soft-tissue sarcomas, common solid tumors of adults such as head and neck cancers (e.g. oral, laryngeal and esophageal), genitourinary cancers (e.g. prostate, bladder, renal, uterine, ovarian, testicular), lung cancer (e.g. small cell carcinoma and non-small cell lung carcinoma, including squamous cell carcinoma and adenocarcinoma), breast cancer, pancreatic cancer, melanoma and other skin cancers, basal cell carcinoma, metastatic skin carcinoma, squamous cell carcinoma of both ulcerating and papillary type, stomach cancer, brain cancer, liver cancer, adrenal cancer, kidney cancer, thyroid cancer, medullary carcinoma, osteosarcoma, soft-tissue sarcoma, Ewing's sarcoma, reticulum cell sarcoma, and Kaposi's sarcoma. Also included are pediatric forms of any of the cancers described herein. Also included are all forms of cancer that have displayed resistance to all currently used drugs.

The most preferred pathology treated with the peptides of the invention is ovarian cancer.

Therefore, the peptides are preferably used to inhibit ovarian cancer cell growth and treat ovarian cancer.

Ovarian cancer is a severe pathology threatening women's lives because of the late diagnosis and of the rapid development of drug resistance to different drugs, in particular to platinum-derived drugs. Cross-resistance of platinum drugs with classical drugs targeting the folate pathway is limiting the access to therapy.

The peptides of the invention represent medicaments with a new mechanism of action against the folate pathway that are effective to reverse ovarian cancer cell resistance to common anticancer drugs, preferably platinum derived drugs, more preferably cisplatin.

For the treatment of ovarian cancer and/or to recover sensitivity of ovarian cancer cell to known anticancer medicaments, the peptides of the invention can be administered, to a patient in need thereof, with or without other chemotherapeutic agents.

For example, the peptides can be used for combination therapy of ovarian cancer together with platinum drugs to reduce drug resistance and provide more effective anti-cancer therapy.

In another embodiment, the peptides of the invention comprise or consist essentially of from 3 to 10, preferably from 4 to 8 amino acids, wherein the sequences of said peptides are chosen in the group consisting of SEQ ID NO: 1-185.

The sequences of the invention have been compiled according to the international standard WIPO standard ST.25; the sequence listings have been developed with the program Patent-In 3.3.

The sequences of the invention and their respective sequence ID numbers are listed in the following Table 1:

| Sequence ID Number | AA Sequence |
|---|---|
| SEQ ID 1 | DFIHTLGD |
| SEQ ID 2 | Ac-DFIHTLGD |
| SEQ ID 3 | DFIHTLGD-NH$_2$ |
| SEQ ID 4 | Ac-DFIHTLGD-NH$_2$ |
| SEQ ID 5 | AFIHTLGD |
| SEQ ID 6 | DAIHTLGD |
| SEQ ID 7 | DFAHTLGD |
| SEQ ID 8 | DFIATLGD |
| SEQ ID 9 | DFIHALGD |
| SEQ ID 10 | DFIHTAGD |
| SEQ ID 11 | DFIHTLAD |
| SEQ ID 12 | DFIHTLGA |
| SEQ ID 13 | FIHTLGD |
| SEQ ID 14 | IHTLGD |
| SEQ ID 15 | HTLGD |
| SEQ ID 16 | DFIHTLG |
| SEQ ID 17 | DFIHTL |
| SEQ ID 18 | DFIHT |
| SEQ ID 19 | FIHTL |
| SEQ ID 20 | IHTLG |
| SEQ ID 21 | LKYVWNPL |
| SEQ ID 22 | LKYVCNPL |
| SEQ ID 23 | VKYVSQSI |
| SEQ ID 24 | LSCQLYQR |
| SEQ ID 25 | ASCQLYQR |
| SEQ ID 26 | LACQLYQR |
| SEQ ID 27 | LSAQLYQR |
| SEQ ID 28 | LSCALYQR |
| SEQ ID 29 | LSCQAYQR |
| SEQ ID 30 | LSCQLYQR |
| SEQ ID 31 | LSCQLYAR |
| SEQ ID 32 | LSCQLYQA |
| SEQ ID 33 | SCQLYQR |
| SEQ ID 34 | CQLYQR |
| SEQ ID 35 | QLYQR |
| SEQ ID 36 | LSCQLYQ |
| SEQ ID 37 | LSCQLY |
| SEQ ID 38 | LSCQL |
| SEQ ID 39 | SCQLY |
| SEQ ID 40 | CQLYQ |
| SEQ ID 41 | LSSQLYQR |
| SEQ ID 42 | DRTVDMVS |
| SEQ ID 43 | QGALQVLS |
| SEQ ID 44 | YVVNSELS |
| SEQ ID 45 | AVVNSELS |
| SEQ ID 46 | YAVNSELS |
| SEQ ID 47 | YVANSELS |
| SEQ ID 48 | YVVASELS |
| SEQ ID 49 | YVVNAELS |
| SEQ ID 50 | YVVNSALS |
| SEQ ID 51 | YVVNSEAS |
| SEQ ID 52 | YVVNSELA |
| SEQ ID 53 | VVNSELS |
| SEQ ID 54 | VNSELS |
| SEQ ID 55 | NSELS |
| SEQ ID 56 | YVVNSEL |
| SEQ ID 57 | YVVNSE |
| SEQ ID 58 | YVVNS |
| SEQ ID 59 | VVNSE |
| SEQ ID 60 | VNSEL |
| SEQ ID 61 | IHHLSLDR |
| SEQ ID 62 | IHHVTLQG |
| SEQ ID 63 | CQLYQRSG |
| SEQ ID 64 | AQLYQRSG |
| SEQ ID 65 | CALYQRSG |
| SEQ ID 66 | CQAYQRSG |
| SEQ ID 67 | CQLAQRSG |
| SEQ ID 68 | CQLYARSG |
| SEQ ID 69 | CQLYQASG |
| SEQ ID 70 | CQLYQRAG |
| SEQ ID 71 | CQLYQRSA |
| SEQ ID 72 | QLYQRSG |
| SEQ ID 73 | LYQRSG |
| SEQ ID 74 | YQRSG |
| SEQ ID 75 | CQLYQRS |

-continued

| Sequence ID Number | AA Sequence |
|---|---|
| SEQ ID 76 | CQLYQR |
| SEQ ID 77 | CQLYQ |
| SEQ ID 78 | QLYQR |
| SEQ ID 79 | LYQRS |
| SEQ ID 80 | SQLYQRSG |
| SEQ ID 81 | TVDMVSSP |
| SEQ ID 82 | ALQVLSRS |
| SEQ ID 83 | QFYVVNSE |
| SEQ ID 84 | VNSELSCQ |
| SEQ ID 85 | SELSCQLY |
| SEQ ID 86 | LCQFYVVN |
| SEQ ID 87 | ACQFYVVN |
| SEQ ID 88 | LAQFYVVN |
| SEQ ID 89 | LCAFYVVN |
| SEQ ID 90 | LCQAYVVN |
| SEQ ID 91 | LCQFAVVN |
| SEQ ID 92 | LCQFYAVN |
| SEQ ID 93 | LCQFYVAN |
| SEQ ID 94 | LCQFYVVA |
| SEQ ID 95 | CQFYVVN |
| SEQ ID 96 | QFYVVN |
| SEQ ID 97 | FYVVN |
| SEQ ID 98 | LCQFYVV |
| SEQ ID 99 | LCQFYV |
| SEQ ID 100 | LCQFY |
| SEQ ID 101 | CQFYV |
| SEQ ID 102 | QFYVV |
| SEQ ID 103 | LSQFYVVN |
| SEQ ID 104 | ETVKIHHL |
| SEQ ID 105 | EALEIHHV |
| SEQ ID 106 | PPCHA |
| SEQ ID 107 | PPSHA |
| SEQ ID 108 | GGTVR |
| SEQ ID 109 | RWAMG |
| SEQ ID 110 | DDRTGTGT |
| SEQ ID 111 | LLACPWPW |
| SEQ ID 112 | VVARAGAG |
| SEQ ID 113 | VDQ |
| SEQ ID 114 | QLV |
| SEQ ID 115 | NVL |
| SEQ ID 116 | DDR |
| SEQ ID 117 | LLS |
| SEQ ID 118 | VVS |
| SEQ ID 119 | RIIMC |
| SEQ ID 120 | RIIMS |
| SEQ ID 121 | SYYYT |
| SEQ ID 122 | SDDHA |
| SEQ ID 123 | VRK |
| SEQ ID 124 | QSF |
| SEQ ID 125 | DPL |
| SEQ ID 126 | SVFGMQ |
| SEQ ID 127 | SHKPYV |
| SEQ ID 128 | RYEAHL |
| SEQ ID 129 | WNPRDL |
| SEQ ID 130 | TLGSLE |
| SEQ ID 131 | PIWSIK |
| SEQ ID 132 | DDRRIIMC |
| SEQ ID 133 | DDRRIIMS |
| SEQ ID 134 | LLSSYYYT |
| SEQ ID 135 | VVSSDDHA |
| SEQ ID 136 | RDWRKGKH |
| SEQ ID 137 | IICWCCGV |
| SEQ ID 138 | NWGGCIKR |
| SEQ ID 139 | RGCRTCVC |
| SEQ ID 140 | CWGMDCRD |
| SEQ ID 141 | CRKRIDWW |
| SEQ ID 142 | CCRGGFII |
| SEQ ID 143 | DCDCIGEW |
| SEQ ID 144 | WRDIYGCW |
| SEQ ID 145 | RIRRWRRI |
| SEQ ID 146 | GDKKGDRV |
| SEQ ID 147 | LRKCRRDD |
| SEQ ID 148 | RIGRGICR |
| SEQ ID 149 | GGGGKILW |
| SEQ ID 150 | GCDWGKHR |
| SEQ ID 151 | EWKERWGW |

| Sequence ID Number | AA Sequence |
|---|---|
| SEQ ID 152 | IWIGWDGW |
| SEQ ID 153 | WIRDGVGG |
| SEQ ID 154 | RGKCWCCR |
| SEQ ID 155 | RDWCCFGR |
| SEQ ID 156 | CKCDMWKW |
| SEQ ID 157 | RDGVWRCE |
| SEQ ID 158 | WDIRDWFW |
| SEQ ID 159 | CCCCRWWA |
| SEQ ID 160 | GWKWCIWC |
| SEQ ID 161 | GRVIICGK |
| SEQ ID 162 | FHGDRHIR |
| SEQ ID 163 | CERRDIDK |
| SEQ ID 164 | GVILRIDC |
| SEQ ID 165 | HWWWGFCW |
| SEQ ID 166 | NVWVRRIR |
| SEQ ID 167 | CGRWPGGC |
| SEQ ID 168 | WCRWWFWG |
| SEQ ID 169 | IKILGWDW |
| SEQ ID 170 | WGWGILKR |
| SEQ ID 171 | WCVWIRRY |
| SEQ ID 172 | DGGWCRGI |
| SEQ ID 173 | WGRINWRF |
| SEQ ID 174 | RRMCWLRG |
| SEQ ID 175 | RRGWVIIP |
| SEQ ID 176 | GGFDVDDD |
| SEQ ID 177 | IPCKWRGC |
| SEQ ID 178 | ILDRCRWD |
| SEQ ID 179 | WCRGGCFC |
| SEQ ID 180 | CRDKVWGG |
| SEQ ID 181 | GIKRWFIR |
| SEQ ID 182 | ICVRIVCI |
| SEQ ID 183 | CFIFIGWL |
| SEQ ID 184 | IKWCGGVK |
| SEQ ID 185 | CDCIRGGR |
| SEQ ID 186 (ht-hTS; FIG. 1) | MRGSHHHHHHGSMPVAGSELPRRPLP PAAQERDAEPRP PHGELQYLGQIQHILRCGVRKDDRTGTGT LSVFGMQARYSLRDEFPLLTTKRVFWKGV LEELLWFIKGSTNAKELSSKGVKIWD ANGSRDFLDSLGFSTREEGDLGPVYGFQW RHFGAEYRDMESDYSGQGVDQLQRVIDTIKT NPDDRRIIMCAWNPRDLPLMALPPCHALCQFYVVN SELSCQLYQRSGDMGLGVPFNIASY ALLTYMIAHITGLKPGDFIHTLGDAHIYLNH IEPLKIQLQREPRPFPKLRILRKVEKIDD FKAEDFQIEGYNPHPTIKMEMAV |

Among the peptides of SEQ ID NO: 1-185 more preferred are those that show an inducible secondary structure.

More preferably the peptides are chosen among the group consisting of: SEQ ID NO: 1-23, SEQ ID NO: 24-43, SEQ ID NO: 44-62, SEQ ID NO: 63-82, SEQ ID NO: 83-85, SEQ ID NO: 86-105, SEQ ID NO: 106-109, SEQ ID NO: 110-112, SEQ ID NO: 113-115, SEQ ID NO: 116-118, SEQ ID NO: 119-122, SEQ ID NO: 123-125, SEQ ID NO: 126-128, SEQ ID NC: 129-131, SEQ ID NO: 132-135 and SEQ ID NO: 136-185.

In a preferred embodiment, the peptides of the invention comprise or consist of eight amino acids with a sequence chosen among the group consisting of SEQ ID NO: 1, SEQ ID NO: 24, SEQ ID NO: 44, SEQ ID NO: 63, SEQ ID NO: 83, SEQ ID NO: 84, SEQ ID NO: 85 and SEQ ID NO: 86.

A preferred peptide is SEQ ID NO: 1 or SEQ ID NO: 24.

The peptides can also be chosen in the group consisting of SEQ ID NO: 2, SEQ ID NO: 3 and SEQ ID NO: 4; these peptides are derivatives of peptide of SEQ ID NO: 1, in which amino-, carboxyl- and amino+carboxyl ends, respectively, are modified by acetylation and amidation.

In another embodiment, the peptides comprise or consist of eight amino acids with a sequence chosen among the group consisting of SEQ ID NO: 1, SEQ ID NO: 5, SEQ ID NO: 6, SEQ ID NO: 7, SEQ ID NO: 8, SEQ ID NO: 9, SEQ ID NO: 10, SEQ ID NO: 11 and SEQ ID NO: 12.

SEQ ID NO: 5 to 12 are obtained from alanine scanning of SEQ ID NO: 1.

In a further embodiment, the peptides comprise or consist of from 5 to 8 amino acids with a sequence chosen in the group consisting of SEQ ID NO: 1, SEQ ID NO: 13, SEQ ID NO: 14, SEQ ID NO: 15, SEQ ID NO: 16, SEQ ID NO: 17, SEQ ID NO: 18, SEQ ID NO: 19 and SEQ ID NO: 20.

SEQ ID NO: 13-20 are derived from progressive shortening of SEQ ID NO: 1.

In another embodiment, the peptides comprise or consist of eight amino acids with a sequence chosen among the group consisting of SEQ ID NO: 1, SEQ ID NO: 21, SEQ ID NO: 22 and SEQ ID NO: 23.

SEQ ID NO: 21-23 are complement or reverse complement peptides of SEQ ID NO: 1.

In another embodiment, the peptides comprise or consist of eight amino acids with a sequence chosen in the group consisting of SEQ ID NO: 24, SEQ ID NO: 25-31 and SEQ ID NO: 32.

SEQ ID NO: 25-32 are obtained from alanine scanning of SEQ ID NO: 24.

In another embodiment, the peptides comprise or consist of from 5 to 8 amino acids with a sequence chosen in the group consisting of SEQ ID NO: 24, SEQ ID NO: 33-39 and SEQ ID NO: 40.

SEQ ID NO: 33-40 are obtained from progressive shortening of SEQ ID NO: 24.

In another embodiment, the peptides comprise or consist of eight amino acids with a sequence chosen among the group consisting of SEQ ID NO: 24, SEQ ID NO: 41, SEQ ID NO: 42 and SEQ ID NO: 43.

SEQ ID NO: 41 is obtained from cysteine substitution with serine of SEQ ID NO: 24 and SEQ ID NO: 42-43 are complement and reverse complement peptides of SEQ ID NO: 24, respectively.

In an alternative form, the peptides of the invention comprise or consist of eight amino acids with a sequence chosen among the group consisting of SEQ ID NO: 44, SEQ ID NO: 45-51, and SEQ ID NO: 52.

SEQ ID NO: 45-52 are obtained from alanine scanning of SEQ ID NO: 44.

In another embodiment, the peptides comprise or consist of from 5 to 8 amino acids with a sequence chosen in the group consisting of SEQ ID NO: 44, SEQ ID NO: 53-59 and SEQ ID NO: 60.

SEQ ID NO: 53-60 are obtained from progressive shortening of SEQ ID NO: 44.

In another embodiment, the peptides comprise or consist of eight amino acids with a sequence chosen among the group consisting of SEQ ID NO: 44, SEQ ID NO: 61 and SEQ ID NO: 62.

SEQ ID NO: 61-62 are complement and reverse complement peptides of SEQ ID NO: 44, respectively.

In an alternative form, the peptides of the invention comprise or consist of eight amino acids with a sequence chosen among the group consisting of SEQ ID NO: 63, SEQ ID NO: 64-70, and SEQ ID NO: 71.

SEQ ID NO: 64-71 are obtained from alanine scanning of SEQ ID NO: 63.

In another embodiment, the peptides comprise or consist of from 5 to 8 amino acids with a sequence chosen in the group consisting of SEQ ID NO: 63, SEQ ID NO: 72-78 and SEQ ID NO: 79.

SEQ ID NO: 72-79 are obtained from progressive shortening of SEQ ID NO: 63.

In another embodiment, the peptides comprise or consist of eight amino acids with a sequence chosen among the group consisting of SEQ ID NO: 63, SEQ ID NO: 80, SEQ ID NO: 81 and SEQ ID NO: 82.

SEQ ID NO: 80 is obtained from cysteine substitution with serine of SEQ ID NO: 63 and SEQ ID NO: 81-82 are complement and reverse complement peptides of SEQ ID NO: 63, respectively.

In an alternative form, the peptides of the invention comprise or consist of eight amino acids with a sequence chosen among the group consisting of SEQ ID NO: 86, SEQ ID NO: 87-93, and SEQ ID NO: 94.

SEQ ID NO: 87-94 are obtained from alanine scanning of SEQ ID NO: 86.

In another embodiment, the peptides comprise or consist of from 5 to 8 amino acids with a sequence chosen in the group consisting of SEQ ID NO: 86, SEQ ID NO: 95-101 and SEQ ID NO: 102.

SEQ ID NO: 95-102 are obtained from progressive shortening of SEQ ID NO: 86.

In another embodiment, the peptides comprise or consist of eight amino acids with a sequence chosen among the group consisting of SEQ ID NO: 86, SEQ ID NO: 103, SEQ ID NO: 104 and SEQ ID NO: 105.

SEQ ID NO: 103 is obtained from cysteine substitution with serine of SEQ ID NO: 86 and SEQ ID NO: 104-105 are complement and reverse complement peptides of SEQ ID NO: 86, respectively.

The peptides of the invention can also comprise or consist of five amino acids with a sequence chosen in the group consisting of SEQ ID NO: 106-109; or comprise or consist of eight amino acids with a sequence chosen among SEQ ID NO: 110-112; or comprise or consist of three amino acids with a sequence chosen among SEQ ID NO: 113-118 or SEQ ID NO: 123-125; or comprise or consist of five amino acids with a sequence chosen among SEQ ID NO: 119-122; or comprise or consist of six amino acids with a sequence chosen among SEQ ID NO: 126-131; or comprise or consist of eight amino acids with a sequence chosen among SEQ ID NO: 132-135.

In another embodiment, the peptides comprise or consist of eight amino acids with a sequence chosen among the group consisting of SEQ ID NO: 136-185.

In a further embodiment, at least two of the above peptides of SEQ ID NO: 1-185 are bound through at least a covalent bond to give "cross-linked" peptides that are useful in the treatment of cancer and to reverse cancer drug resistance.

For example, SEQ ID NO: 1 can be bound to SEQ ID NO: 126, through at least a covalent bond, to give a "cross-linked" peptide.

Other examples of such "cross-linked" peptides are: SEQ ID NO: 1-SEQ ID NO: 63; SEQ ID NO: 1-SEQ ID NO: 80; SEQ ID NO: 24-SEQ ID NO: 86; SEQ ID NO: 24-SEQ ID NO: 103; SEQ ID NO: 103-SEQ ID NO: 119; SEQ ID NO: 103-SEQ ID NO: 120; SEQ ID NO: 86-SEQ ID NO: 119, SEQ ID NO: 86-SEQ ID NO: 120.

The peptides having the above sequences can be used to treat cancer, especially ovarian cancer. The peptides can also be employed to reverse drug resistance to known anticancer medicines, in particular to platinum derived drugs.

The peptides described herein can be used also to target other Thymidylate synthase proteins, preferentially Thymidylate synthase of *Escherichia coli* (EcTS), *Enterobacter faecalis* (EfTS), *Pneumocistis carinii* (PcTS) or *Criptococcus neoformans* (CnTS).

The identity, homology and diversity degree between the sequences of Thymidylate synthase of these organisms and the human one, have been evaluated using commercially available algorithms, and as shown in Table 3, the found values are highly significant.

TABLE 3

|  |  | Criptococcus neoformans TS | Enterobacter faecalis TS | Escherichia coli TS | Pneumocistis carinii TS |
| --- | --- | --- | --- | --- | --- |
| Human TS | % Identity | 57 | 42 | 45 | 56 |
|  | % Homology | 70 | 54 | 60 | 70 |
|  | % Diversity | 7 | 21 | 15 | 9 |

Peptides as described herein may comprise residues of L-amino acids, D-amino acids, or any combination thereof.

Amino acids may be from natural or non-natural sources, provided that at least one amino group and at least one carboxyl group are present in the molecule.

The peptides of the invention may also contain one or more rare amino acids (such as 4-hydroxyproline or hydroxylysine) and/or derivatives of common amino acids, such as amino acids having the C-terminal carboxylate esterified (e.g. benzyl, methyl or ethyl ester) or amidated and/or having modifications of the N-terminal amino group (e.g. acetylation or alkoxycarbonylamino), with or without any of a wide variety of side chain modifications and/or substitutions (e.g., methylation, benzylation, t-butylation, tosylation, alkoxycarbonylamino etc.).

Preferred derivatives include amino acids having an N-acetyl group (such that the amino group that represents the N-terminus of the linear peptide is acetylated) and/or a C-terminal amide group (i.e. the carboxy terminus of the linear peptide is amidated)

The peptides of the invention can comprise residues other than common amino acids chosen in the group consisting of penicillamine, tetramethylene cysteine, pentamethylene cysteine, mercaptopropionic acid, pentamethylene-mercaptopropionic acid, 2-mercaptobenzene, 2-mercaptoaniline, 2-mercaptoproline, ornithine, diaminobutyric acid, aminoadipic acid, m-aminomethylbenzoic acid and diaminopropionic acid. The peptides can be coupled to protein carrier molecules in order to facilitate delivery thereof to target cells in vitro (including ex vivo) and in vivo (*Cellular Drug Delivery: Principles and Practice*, edited by Lu, D. R. and Oie, S., Human Press, Totowa, N.J., 2004).

For example, small regions (e.g., 9-16 amino acids) of proteins called protein transduction domains (PTDs) and cell penetrating peptides (CPP) possess the ability to traverse biological membranes through protein transduction (Barnett, E. M. et al., Invest. Opthalmol. Vis. Sci, 2006, 47:2589-2595; Schwarze S. R. et al., Science, 1999, 285(5433): 1569-1572; Wadia, J. S, and Dowdy, S. F., Advanced Drug Delivery Reviews, 2005, 57(4): 579-596; Wadia, J. S, and Dowdy, S. F., Curr. Opin. Biotechnol, 2002, 13(1) 52-56; Ho A. et al., Cancer Research, 2001, 61:474-477; Futaki et al., J. Biol. Chem., 2001, February, 276(8):5836-5840; Cao G. et al., J. Neuroscl, 2002, 22(13): 5423-5431; Becker-Hapk, M. et al, Methods, 2001, 24:247-256; Snyder, E. L. and Dowdy, S. F., Curr. Opin. Mol. Ther., 2001, 3:147-152; Lewin, M. et al., Nat. Biotechnol., 2000, 18:410-414; Tung, C H. et al., Bioorg. Med. Chem., 2002, 10:3609-3614; Richard, J. P., et al., J. Biol. Chem., Oct. 30, 2002, epub ahead of print).

Transduction can occur in a receptor- and transporter-independent fashion that appears to target the lipid bilayer directly.

Proteins (peptides) and compounds that are linked to PTDs (e.g., covalently) have the capability to traverse outer cell membranes.

Preferably, the delivery peptide is a trans-activating transcriptional activator (TAT) peptide or an Antennapedia (ANTP) peptide, or a derivative thereof.

PTDs can be linked to the peptides of the subject invention for transport across the cell membrane. One well characterized PTD is the human immunodeficient virus (HIV)-I Tat peptide (see, for example, U.S. Pat. Nos. 5,804,604; 5,747,641; 5,674,980; 5,670,617; and U.S. Pat. No. 5,652,122). Peptides such as the homeodomain of *Drosophila antennapedia* (ANTP) and arginine-rich peptides that display similar properties can be employed.

VP22, a tegument protein from Herpes simplex virus type 1 (HSV-I), also has the ability to transport proteins across a cell membrane, and may be coupled to the peptides of the invention.

Furthermore, some protein carrier molecules, such as PTDs, may be used to promote efficient delivery of genetic material to cells in vitro (including ex vivo) or in vivo (see, for example, Eguchi A. et al., J. Biochem., 2001 276(28): 26204-26210; Torchilin, V. P. et al., PNAS, 2001, 98(15): 8786-9791).

Such molecules can be coupled to viral and non-viral gene delivery vectors for delivery of nucleic acids encoding peptides such as those of the invention (Lehmusvaara S. et al, BioTechniques, 2006, 40(5): 573-576). TAT-based polyplexes can also been utilized, and should be particularly beneficial in cases that require surface presentation of membrane-active or cell-specific targeting peptides (Manickam D. S. et al., Journal of Controlled Release, 2005, 102:293-306). An example of synthetic vectors that can be used for delivery of the peptides of the invention or nucleic acids encoding the peptides are liposomes.

The delivery of peptides and/or coupled-peptides, as above mentioned, can be realized using transfection reagents, preferably.

Accordingly, in another aspect the present invention relates to polynucleotides comprising nucleotide sequences encoding the peptides of the invention. Polynucleotides can be administered to cells or subjects and expressed in place of the peptides themselves when it is the case.

The invention also provides genetic constructs comprising a polynucleotide sequence of the invention. Genetic constructs of the invention can also contain additional regulatory elements such as promoters and enhancers and, optionally, selectable markers.

In an embodiment, host cells that have been genetically modified with a polynucleotide encoding at least one peptide of the invention are administered to a subject to treat a proliferation disorder and/or to reduce the growth of malignant cells. The polynucleotide is expressed by the host cells, thereby producing the peptides within the subject. Preferably, the host cells are allogenic or autogenic to the subject.

In another embodiment, a targeting agent may also be linked to a peptide of the invention to facilitate targeting to one or more specific tissues.

As used herein, a "targeting agent" may be any substance (such as a compound or cell) that, when linked to a peptide of the invention enhances the transport of the peptide inhibitor to a target tissue, thereby increasing the local concentration of the inhibitor.

Targeting agents include antibodies or fragments thereof, receptors, ligands and other molecules that bind to cells of, or in the vicinity of, the target tissue. Known targeting agents include serum hormones, antibodies against cell surface antigens, lectins, adhesion molecules, tumor cell surface binding ligands, steroids, cholesterol, lymphokines, fibrinolytic enzymes and those drugs and proteins that bind to a desired target site.

For certain embodiments, it may be beneficial to also, or alternatively, link a drug to a peptide of the invention. As used herein, the term "drug" refers to any bioactive agent intended for administration to a human or non-human mammal to prevent or treat a disease or other undesirable condition. Drugs include hormones, growth factors, proteins, peptides and other compounds.

The peptides according to the invention can be administered by various well known routes, including oral, rectal, intragastrical, intracranial and parenteral administration (e.g. intravenous, intramuscular, intranasal, intradermal, subcutaneous), and similar administration routes. Parenteral administration and particular intravenous administration, preferably by depot injection, is preferred. Depending on the route of administration different pharmaceutical formulations are required and some of those may require that protective coatings are applied to the drug formulation to prevent degradation of a compound of the invention in, for example, the digestive tract.

Thus, preferably, a compound of the invention is formulated as a syrup, an infusion or injection solution, a tablet, a capsule, a capslet, lozenge, a liposome, a suppository, a plaster, a band-aid, a retard capsule, a powder, or a slow release formulation. Preferably, the diluent is water, a buffer, a buffered salt solution or a salt solution, and the carrier is preferably selected from the group consisting of cocoa butter and vitebesole.

Particularly preferred pharmaceutical forms for the administration of a compound of the invention are forms suitable for injectionable use and include sterile aqueous solutions or dispersions and sterile powders for the extemporaneous preparation of sterile injectable solutions or dispersion.

In all cases the final solution or dispersion form must be sterile and fluid.

Typically, such a solution or dispersion will include a solvent or dispersion medium, containing, for example, water-buffered aqueous solutions, e.g. biocompatible buffers, ethanol, polyol, such as glycerol, propylene glycol, polyethylene glycol, suitable mixtures thereof, surfactants or vegetable oils.

A compound of the invention can also be formulated into liposomes, in particular for parenteral administration. Liposomes provide the advantage of increased half life in the circulation, if compared to the free drug and a prolonged more even release of the enclosed drug. Sterilization of infusion or injection solutions can be accomplished by any recognized techniques including the addition of preservatives like antibacterial or anti-fungal agents (e.g. parabene, chlorobutanol, phenol, sorbic acid or thimersal). Further, isotonic agents, such as sugars or salts, in particular sodium chloride may be incorporated in infusion or injection solutions. Production of sterile injectable solutions containing one or several of the compounds of the invention is accomplished by incorporating the respective compound, in the required amount, in the appropriate solvent with various ingredients as specified above, followed by sterilization.

To obtain a sterile powder the above solutions are vacuum-dried or freeze-dried as necessary. Preferred diluents of the present invention are water, physiological acceptable buffers, physiological acceptable buffer salt solutions or salt solutions. Preferred carriers are cocoa butter and vitebesole. Excipients which can be used with the various pharmaceutical forms of a compound of the invention can be chosen from the following list:

a) binders, such as lactose, mannitol, crystalline sorbitol, dibasic phosphates, calcium phosphates, sugars, microcrystalline cellulose, carboxymethyl cellulose, hydroxyethyl cellulose, polyvinyl pyrrolidone and the like;

b) lubricants, such as magnesium stearate, talc, calcium stearate, zinc stearate, stearic acid, hydrogenated vegetable oil, leucine, glycerides and sodium stearyl fumarates;

c) disintegrants, such as starches, croscaramellose, sodium methyl cellulose, agar, bentonite, alginic acid, carboxymethyl cellulose and polyvinyl pyrrolidone.

Other suitable excipients can be found in the Handbook of Pharmaceutical Excipients, published by the American Pharmaceutical Association.

It is to be understood that depending on the severity of the disorder and the particular type which is treatable with one of the compounds of the invention, as well as on the respective patient to be treated (e.g. the general health status of the patient, etc.) different doses of the respective compound are required to elicit a therapeutic or prophylactic effect. The determination of the appropriate dose lies within the discretion of the attending physician. It is contemplated that the dosage of a compound of the invention in the therapeutic or prophylactic use of the invention should be in the range of about 0.1 mg to about 1 g serum per kg body weight.

However, in a preferred use of the present invention a compound of the invention is administered to a subject in need thereof in an amount ranging from 1.0 to 500 mg/kg body weight, preferably ranging from 10 to 200 mg/kg body weight, preferably ranging from 50 to 150 mg/kg body weight, preferably ranging from 90 to 100 mg/kg body weight. The duration of therapy with a compound of the invention will vary, depending on the severity of the disease being treated and the condition and idiosyncratic response of each individual patient.

As is known in the art, the pharmaceutically effective amount of a given composition will also depend on the administration route. In general the required amount will be higher, if the administration is through the gastrointestinal tract (e.g. by suppository, rectal, or by an intragastric probe) and lower if the route of administration is parenteral (e.g. intravenous). Typically, a compound of the invention will be administered in ranges of 50 mg to 1 g/kg body weight, preferably 100 mg to 500 mg/kg body weight, if rectal or intragastric administration is used, and in ranges of 10 to 100 mg/kg body weight, if parenteral administration is used.

If a person is known to be at risk of developing a disorder treatable with a compound of the invention, a prophylactic administration of the pharmaceutical composition according to the invention may be possible. In these cases the respective compound of the invention is preferably administered in the above outlined preferred and particular preferred doses on a daily basis. Preferably, between 0.1 mg to 1 g/kg body weight once a day, preferably 10 to 200 mg/kg body weight. This administration can be continued until the risk of developing the respective disorder has lessened.

In most instances, however, a compound of the invention will be administered once a disease/disorder has been diagnosed. In these cases it is preferred that a first dose of a compound of the invention is administered one, two, three or four times daily. Preferably the administration is discontinued for one day, one week or one month and then repeated until the symptoms of the respective disease are no longer worsening or improving.

The peptide compounds of the invention are synthesized using methods well known in the art, including recombinant DNA methods and chemical synthesis.

Chemical synthesis may generally be performed using standard solution phase or solid phase peptide synthesis techniques, in which a peptide linkage occurs through the direct condensation of the amino group of one amino acid with the carboxy group of the other amino acid with the elimination of a water molecule. Peptide bond synthesis by direct condensation, as formulated above, requires suppression of the reactive character of the amino group of the first and of the carboxyl group of the second amino acid. The masking substituents must permit their ready removal, without inducing breakdown of the labile peptide molecule.

In solution phase synthesis, a wide variety of coupling methods and protecting groups may be used (see Gross and Meienhofer, "The Peptides: Analysis, Synthesis, Biology," Vol. 1-4; Academic Press, 1979; Bodansky and Bodansky, "The Practice of Peptide Synthesis," 2d ed. (Springer Verlag, 1994)).

In addition, intermediate purification and linear scale up are possible. Those of ordinary skill in the art will appreciate that solution synthesis requires consideration of main chain and side chain protecting groups and activation method.

In addition, careful segment selection is necessary to minimize racemization during segment condensation. Solubility considerations are also a factor. Solid phase peptide synthesis uses an insoluble polymer for support during organic synthesis. The polymer-supported peptide chain permits the use of simple washing and filtration steps instead of laborious purifications at intermediate steps. Solid-phase peptide synthesis may generally be performed according to the method of Merrifield et al., J. Am. Chem. Soc, 1963, 85:2149, which involves assembling a linear peptide chain on a resin support using protected amino acids. Solid phase peptide synthesis typically utilizes either the Boc or Fmoc strategy, which are well known in the art.

Those of ordinary skill in the art will recognize that, in solid phase synthesis, deprotection and coupling reactions must go to completion and the side-chain blocking groups must be stable throughout the synthesis. In addition, solid phase synthesis is generally most suitable when peptides are to be made on a small scale.

Acetylation of the N-terminal can be accomplished by reacting the final peptide with acetic anhydride before cleavage from the resin. C-amidation is accomplished using an appropriate resin such as methylbenzhydrylamine resin using the Boc technology.

The peptides disclosed herein may be modified by attachment of a second molecule that confers a desired property upon the peptide, such as increased half-life in the body, for example, pegylation.

Covalent attachment of a molecule or solid support may generally be achieved by first reacting the support material with a bifunctional reagent that will also react with a functional group, such as a hydroxyl, thiol, carboxyl, ketone or amino group, on the modulating agent. A preferred method of generating a linkage is via amino groups using glutaraldehyde. A peptide may be linked to cellulose via ester linkages. Similarly, amide linkages may be suitable for linkage to other molecules such as keyhole limpet hemocyanin or other support materials.

EXAMPLES

Example 1

Human TS Inhibition by Peptide a) Peptides Synthesis:

Peptides of SEQ ID NO: 1-185 are synthesized through the classical Fmoc automated protocol. The purification of peptides was done by reverse phase HPLC with U.V. detection at 220 nm. The level of purity of the product was >95%. Each purified peptide was systematically analysed through mass spectrometry. The peptides were further purified before use to eliminate the trifluoroacetic acid.

b) Protein Cloning and Purification:

Human Thymidylate synthase was purified from the E. coli BL21 strain DH5α transformed with pQE80L, which contains the complete coding sequence for the human Thymidylate Synthase (hTS) tagged with a histidine tail. Purification involved sequential chromatography on Ni Sepharose Fast Flow resin column and HiTrap desalting column, both from GE Healthcare.

c) Enzyme Kinetics:

Peptidic Inhibitor Enzymatic Inhibition Assay.

hTS enzyme (~300 nM) has been incubated in MilliQ water for one hour at 25° C. in presence of a fixed concentration of the following inhibitors: SEQ ID NO: 1-18, SEQ ID NO: 24, SEQ ID NO: 41, SEQ ID NO: 44, SEQ ID NO: 63, SEQ ID NO: 80, SEQ ID NO: 83, SEQ ID NO: 84, SEQ ID NO: 85 and SEQ ID NO: 86, SEQ ID NO: 103. After that the reaction mixture volume was doubled by addition of TES buffer. Subsequently, mTHF and dUMP were added at a final concentration of 60 µM and 120 µM, respectively; the reaction has been monitored through UV absorbance at 340 nm for 180 seconds.

Final concentration of the inhibitors was 100 µM.

Peptidic Inhibitor Ki Value Determination Vs dUMP.

hTS enzyme (~300 nM) has been incubated in MilliQ water for one hour at 25° C. in presence of dUMP at increasing concentrations and of a fixed concentration of the following inhibitors: SEQ ID NO: 1-18, SEQ ID NO: 24, SEQ ID NO: 41, SEQ ID NO: 44, SEQ ID NO: 63, SEQ ID NO: 80, SEQ ID NO: 83, SEQ ID NO: 84, SEQ ID NO: 85 and SEQ ID NO: 86, SEQ ID NO: 103. After that the reaction mixture volume was doubled by addition of TES buffer. Subsequently, mTHF was added at a final concentration of 60 µM; the reaction has been monitored through UV absorbance at 340 nm for 180 seconds.

Final concentrations of dUMP were 10.725, 21.45, 42.90, 85.80, 171.60 and 203.77 µM while concentrations of the inhibitors were 0, 50 and 100 µM.

Peptidic Inhibitor Ki Value Determination Vs mTHF.

hTS enzyme (~300 nM) has been incubated in MilliQ water for one hour at 25° C. in presence of mTHF at increasing concentrations and of a fixed concentration of the following inhibitors: SEQ ID NO: 1-18, SEQ ID NO: 24, SEQ ID NO: 41, SEQ ID NO: 44, SEQ ID NO: 63, SEQ ID NO: 80, SEQ ID NO: 83, SEQ ID NO: 84, SEQ ID NO: 85 and SEQ ID NO: 86, SEQ ID NO: 103. After that the reaction mixture volume was doubled by addition of TES buffer. Subsequently, dUMP was added at a final concentration of 120 µM; the reaction has been monitored through UV absorbance at 340 nm for 180 seconds.

Figure 2:
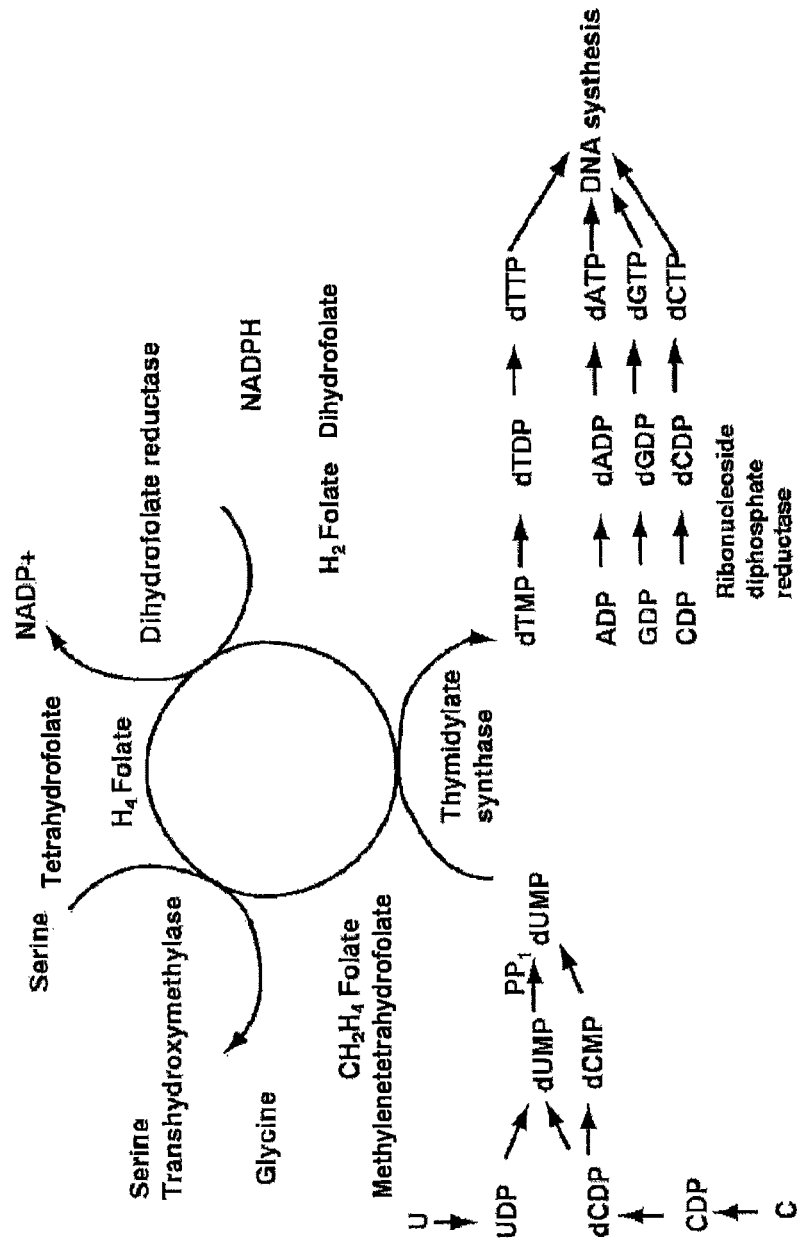
FIG. 2 shows the known Thymidylate synthase cycle.
Figure 3:
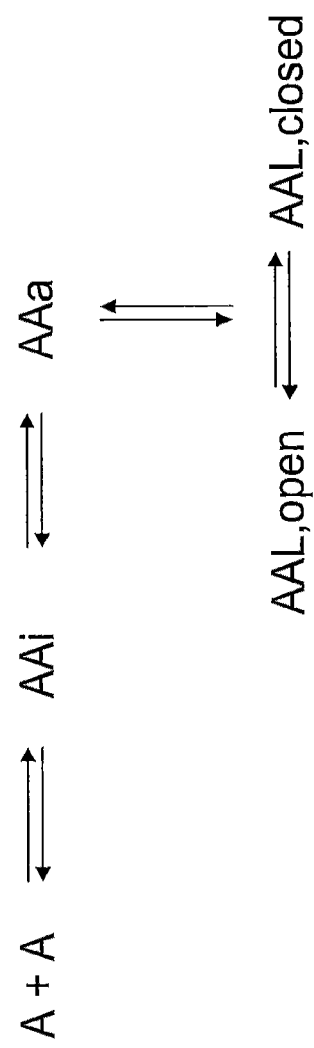
FIG. 3 shows a model of the known equilibrium described for human TS, based on experimental data; A is the monomeric form, AAi is the dimeric inactive form, AAa is the dimeric active form, AAL,open is the dimeric bound open form and AAL,closed is the dimeric bound closed form.
Figure 4:
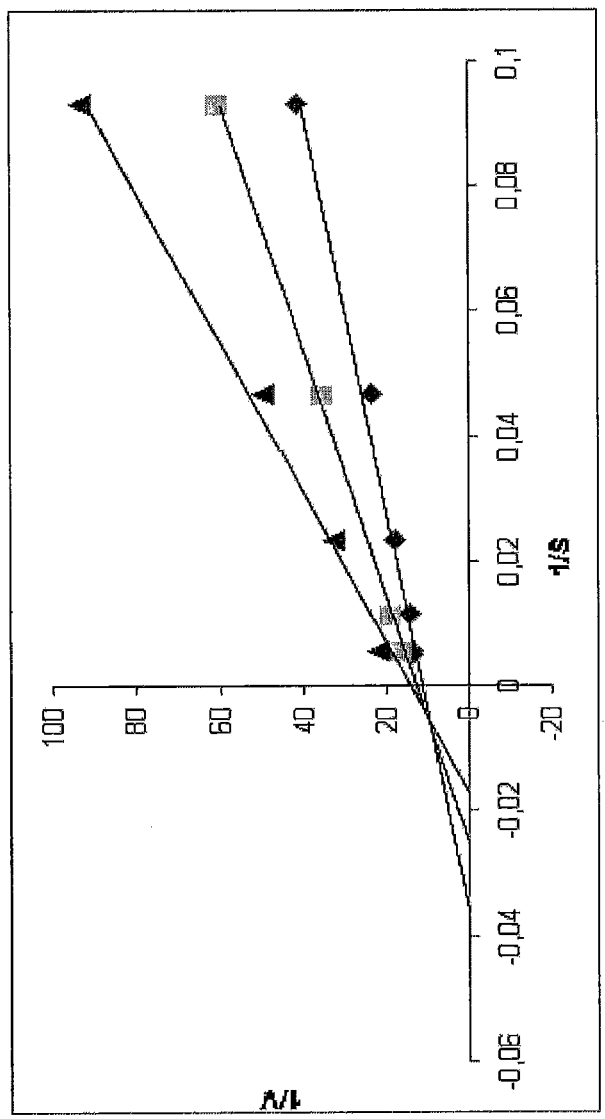
FIG. 4 shows the Lineweaver-Burk inhibition plot of the peptide corresponding to SEQ ID NO: 24.

Final concentrations of mTHF were 9.64, 19.28, 41.76, 80.31 and 118.86 µM while concentrations of the inhibitors were 0, 50 and 100 µM.

d) Results:

Kinetic experiments were performed to study the inhibition properties of the peptides. The specificity of the peptide binding was evaluated by testing the interaction of SEQ ID NO: 1-18, SEQ ID NO: 24, SEQ ID NO: 41, SEQ ID NO: 44, SEQ ID NO: 63, SEQ ID NO: 80, SEQ ID NO: 83, SEQ ID NO: 84, SEQ ID NO: 85 and SEQ ID NO: 86, SEQ ID NO: 103 with hTS. hTS is inhibited by all of the tested peptides showing $K_i$ in the range of 3 µM-400 µM where SEQ ID NO: 1 showed $K_i$ of 30 µM. The analysis of the kinetic data indicate a mixed type inhibition in the case of peptides SEQ ID NO: 24, SEQ ID NO: 63 and SEQ ID NO: 86, while SEQ ID NO: 1 shows a competitive inhibition pattern ((see FIG. 4 for SEQ ID NO: 24 as an example).

Figure 5:
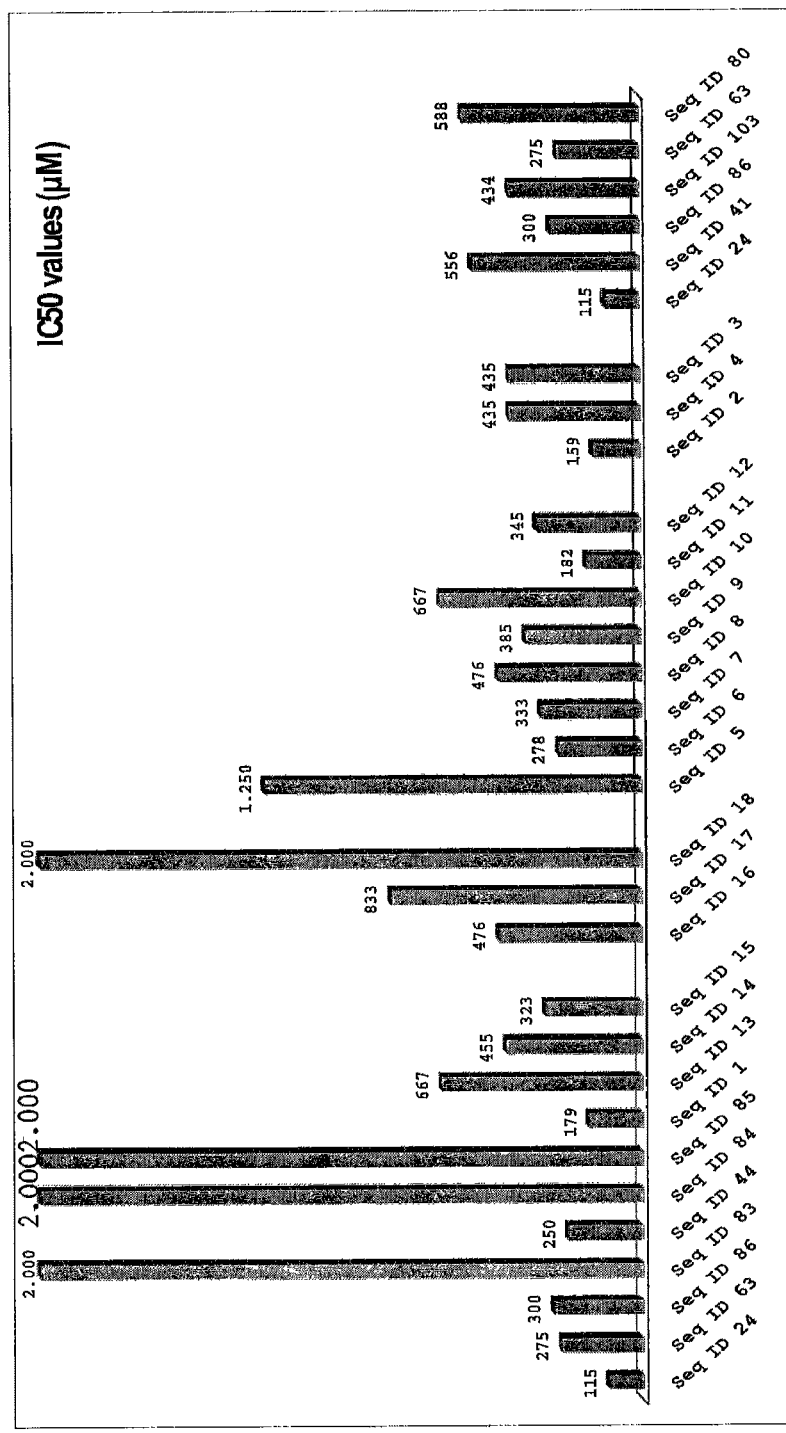
FIG. 5 shows the inhibitory activity (IC50 values) of the peptides of the invention against human TS.

In FIG. 5, the IC50 (concentration of the peptide that reduces the enzyme activity to 50%) of the mentioned peptides have been reported. These results have shown clearly that a few shorter peptides (with a 4 residues length) maintain the activity of the longer 8-mer peptides. The peptide sequences are part of a beta-hairpin loop in the structure of hTS. To investigate if and which type of secondary structure the peptides may adopt in the unbound state in aqueous solution and if there was a relationship between the propensity to assume a secondary structure and their activity, the authors of the present invention have first studied computationally the conformational properties of the peptides. In molecular dynamics simulations, all the octapeptides were flexible and mostly unstructured though displaying some tendency towards helical structures. Subsequently, circular dichroism (CD) spectra of the peptides have been measured in water and in the presence of different percentages (0-100%) of the α-helix structure inducer, 2,2,2-trifluoro-ethanol (TFE). The results reveal a correlation between the intrinsic propensity of the peptides to assume secondary structure (α-helix, β-sheet, β-hairpin, PPI) and their activity as hTS inhibitors. Only those peptides that inhibit hTS adopted a secondary structure.

The inhibitory peptides displayed a range of secondary structure types, suggesting that the contribution of a structured unbound conformation may be to reduce the entropy penalty associated with binding to hTS.

Example 2

Docking Study to Determine the Binding Sites of Peptides, Including SEQ ID NO: 24

To investigate how the peptides bind to TS, we used computational docking techniques to dock several peptides, including SEQ ID NO: 24, to the protein. The protein was modelled in active and inactive conformations and in monomeric and dimeric forms. In apo-hTS, the active site was identified as a possible binding site for the peptides. Docking poses were also found at the dimer interface for both the monomeric and dimeric forms. In the former case they were close to Y213 or R175 and R176. In the latter case, they were near the position of the peptide identified crystallographically (Example 5) or in a crevice on the other side of the dimer interface.

Example 3

Effects of Peptides on Cisplatin-Sensitive and -Resistant Cell Lines a) Cell Lines:

The 2008 cell line was established from a patient with serous cystadenocarcinoma of the ovary and the cisplatin (cDDP)-resistant C13* subline, about 15-fold resistant to cDDP, was derived from the parent 2008 cell line. The human ovarian carcinoma A2780/CP cells are 12-fold resistant to cDDP and derived from the parent A2780 cell line. Cells were grown as monolayers in RPMI 1640 medium (Lonza, Verviers, Belgium) containing 10% heat-inactivated fetal bovine serum (Lonza, Verviers, Belgium) and 50 µg/ml gentamycin sulfate. Cultures were equilibrated with humidified 5% $CO_2$ in air at 37° C.

b) Cell Growth Assay

Figure 7:
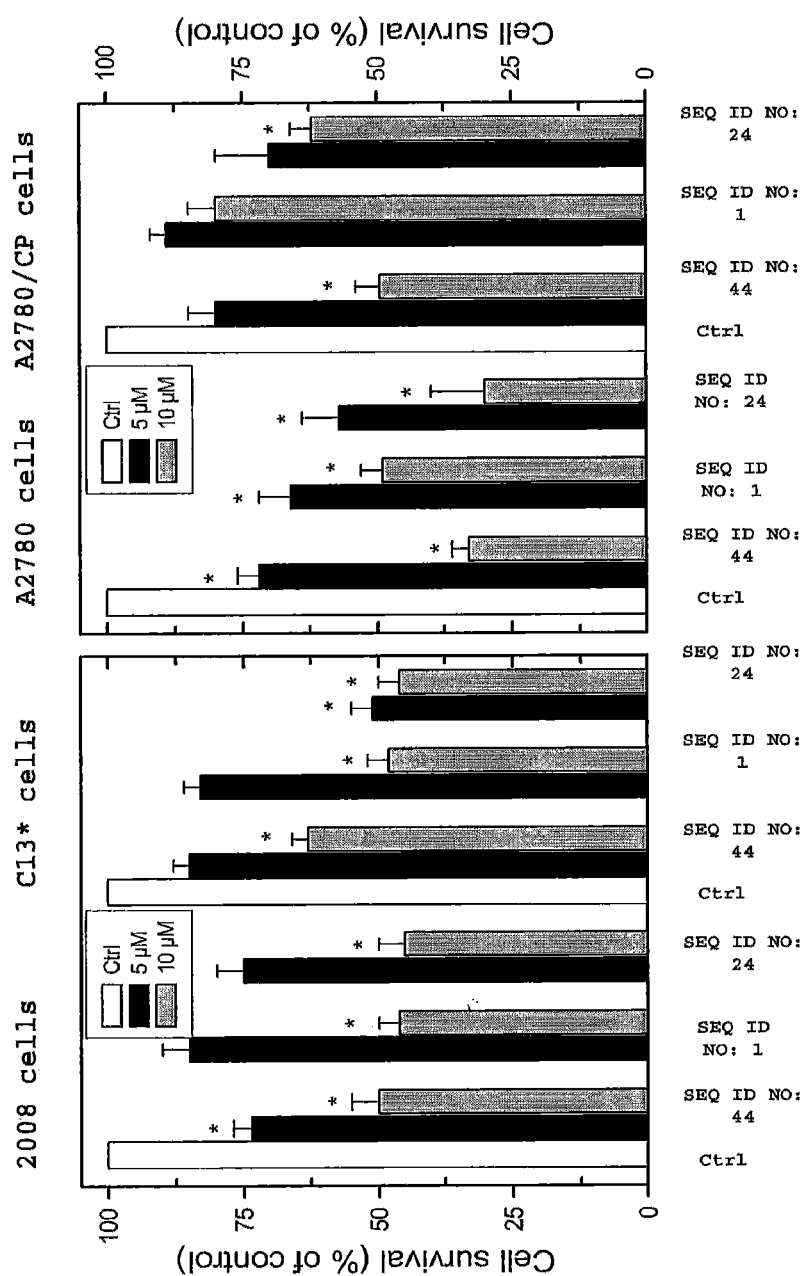
FIG. 7 shows the ovarian cancer cell growth inhibition plot of the peptides SEQ ID NO: 1, 24 and 44 using a peptide delivery system.

Cells were seeded into 24-well plates and allowed to attach overnight. Peptides were delivered into cells by means of a peptide delivery system, following the procedures indicated by the manufacturer. On selected days, after removal of the tissue culture medium, cell growth was determined by a modification of the crystal violet dye assay. The extracted dye was proportional to cell number. Percentage of cytotoxicity was calculated by comparing the absorbance of exposed to non-exposed (control) cultures (see FIG. 7-8)

c) TS Catalytic Assay:

Cells were seeded into 60 mm plates and allowed to attach overnight. Peptides corresponding to SEQ ID NO: 1, SEQ ID NO: 24, SEQ ID NO: 44 were delivered into cells by means of the peptide delivery system, following the procedures indicated by the manufacturer. Cells in an exponential growth phase were then harvested and treated for TS catalytic assay, conducted essentially according to a previously reported method, determining the catalytic activity of TS by measuring the amounts of $^3H$ release from [5-$^3H$]dUMP during its TS catalyzed conversion to dTMP. Briefly, the assay consisted of enzyme suspensions in assay buffer (lysis buffer without Triton X-100), 650 µM 5,10-methylenetetrahydrofolate in a final volume of 50 µl. The reaction was started by adding [5-$^3H$]dUMP (1 µM final concentration, specific activity 5 mCi/mol), incubated for 60 min at 37° C., and stopped by adding 50 µl of ice-cold 35% trichloroacetic acid. Residual [5-$^3H$]dUMP was removed by the addition of 250 µl of 10% neutral activated charcoal. The charcoal was removed by centrifugation at 14,000×g for 15 min at 4° C., and a 150-µl sample of the supernatant was assayed for tritium radioactivity by liquid scintillation counting in the liquid scintillator analyzer Tri-Carb 2100 (Packard). For each cell line, linearity of [5-$^3H$]dUMP conversion with respect to amount of protein and time was established. Protein content in the various assays was estimated by the method of Lowry et al.

All values report the mean±S.E.M, unless otherwise indicated. Statistical significance was estimated by a two-tailed Student's t-test performed using Microsoft Excel Software; a difference was considered to be significant at *$P<0.05$ or **$P<0.01$.

d) Results:

In order to analyze the effects of the peptides on the TS enzyme from human cell lines, at first the authors of the present invention have chosen a cisplatin-sensitive human ovarian cancer cell line, 2008 cells, and its -resistant counterpart C13* cells. Therefore, the cell cultures have been transfected with peptides using a delivery system to verify peptide inhibitory properties. The results obtained showed that 48-h exposure to the maximum amount of peptide delivered by this system, corresponding at about 10 µM, reduced the TS activity of 2008 and C13* cells by 65% and 80%, respectively (data not shown)

Figure 8:
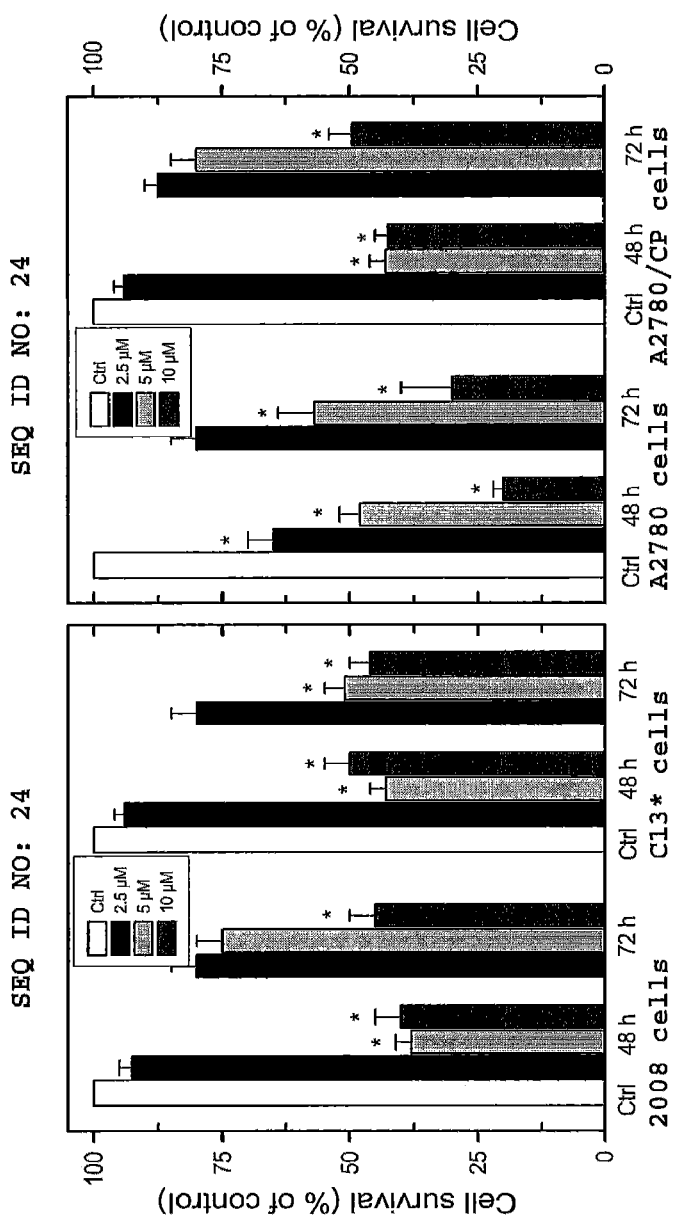
FIG. 8 shows the ovarian cancer cell growth inhibition plot of peptide SEQ ID NO: 24 using a peptide delivery system.

Without transfection by the peptide delivery system, the peptides were very scantly cytotoxic against all cell lines and only at concentrations 10-15-fold higher. The results shown in FIG. 7 indicate that all the three peptides SEQ ID NO: 24, SEQ ID NO: 1 and SEQ ID NO: 44 at 10 µM significantly (*$P<0.05$, n=5) inhibited the growth of both sensitive 2008 and A2780 cells, as well as of resistant C13* and A2780/CP cells by about 50%; even if, SEQ ID NO: 24 and SEQ ID NO: 44 appeared particularly active against A2780 cells. The dose- and time-dependent inhibitory effects of peptide SEQ ID NO: 24 is depicted in FIG. 8. As is evident, the lowest concentration of the peptide is active only against A2780 cell growth, whereas the other two concentrations were cytotoxic towards all cell lines already after 48-h exposure. Again, the effect was more evident in A2780 cells that were killed by about 75% following both 48 h and 72 h exposure. The same peptide caused approximately 50% cell growth inhibition of the other cell lines when compared to the respective untreated control cells.

These peptides were very helpful to identify a previously unexplored binding site that is located at the interface between the two monomers and to discover peptides with a new mechanism of action. The peptides provide an example of inhibitors with the ability to block the inactive form of the protein. The authors of the present invention observed that peptides, that showed an inducible secondary structure, were the same that demonstrated an effective binding and consistently proved an effective capacity to inhibit ovarian cancer cell growth. Some of the peptides tested showed the capacity to reverse the cisplatin drug resistance level when administered through appropriate delivery system. The approach followed was very effective in the identification of active and specific peptides that can cross the cell membrane through a specific mechanism. These compounds represent the important starting point for peptide optimization with in vivo effect.

Example 4

Thermodynamics and Specificity of the Peptides Binding to Human TS a) Isothermal Titration Calorimetry:

The calorimetric experiments were performed on a MicroCal™ VP-ITC Microcalorimeter. Experiments were initiated by filling the reference cell with ca. 1.5 mL of MilliQ water and sample cell with ca. 1.5 mL of a hTS solution (10, 20 and 40 µM) in $NaH_2PO_4$ buffer. After all components of the instrument have reached thermal equilibrium to the desired experimental temperature, identical volumes for each injection of reactant were then injected into the sample titration cell. Injection volume was 10 µL and an equilibrium time of 4 min was allowed between each injection. Total injections number was 28. The heat effect arising from dissolution of the titrant was measured in a separate experiment where the titration cell was filled with buffer. These contributions to the observed heats of reaction were subtracted from corresponding total heats. The heat effect of the enzyme's dilution due to titrant injection was negligible in all cases.

8-mers peptides (SEQ ID NO: 1, SEQ ID NO: 24, SEQ ID NO: 44, SEQ ID NO: 63, SEQ ID NO: 83, SEQ ID NO: 84, SEQ ID NO: 85 and SEQ ID NO: 86.) were dissolved in experimental buffer, at the desired concentration, the day before the experiment leaving them with magnetic stirring at 4° C., O/N. The day of experiment, peptide's solution was filtered with a 0.45 nm filter and the effective concentration was determined by UV measurement. Then, it was loaded in the injection syringe following instrument's instructions. Enzyme solution was filtered with a 0.45 nm filter and then degassed for 8 minutes under magnetic stirring. The solution was then loaded inside the sample cell of the instrument following instructions. After these procedures the injection syringe were positioned and titration started.

b) Results:

Isothermal Titration calorimetry (ITC) was used to study the thermodynamics and specificity of peptide's interaction with human TS. In particular the focus was on peptide of SEQ ID NO: 24 whose X-ray crystallographic structure was obtained. Data obtained from hTS titration with peptide of SEQ ID NO: 24 are consistent with a model that expects the presence of two different protein forms of which only one of them may interact with the peptide. This is the case of hTS which is known to show an equilibrium between active and inactive forms where the inactive form can be converted to active one in the presence of substrates. The model describes a two consecutive, non-identical, binding sites interaction; the first is enthalpically and mildly entropically driven while the second has a larger entropic contribution.

From data analysis, peptide of SEQ ID NO: 24 exhibited a $K_d$ value of $1.51 \times 10^{-7}$ M for the first binding site and $1.28 \times 10^{-6}$ M for the second. The same interaction model has been confirmed for peptide of SEQ ID NO: 63.

The X-ray structure of the hTS-SEQ ID NO: 24 complex shows only one molecule bound in the interface binding site. This model is in agreement with the ITC thermodynamic description in which the first binding domain exerted an enthalpically driven interaction while the second a more entropically one. This second molecule may not crystallize due to the high entropic contribution that characterizes its thermodynamic binding profile.

Normally, the inactive form is converted to active form thanks to substrates. On the basis of nDSC data it has been supposed that the peptide binding stabilizes this inactive form, preventing its conversion and leading to the observed kinetic activity decrease.

Example 5

Crystallization of ht-hTS and the Complex ht-hTS-SEQ ID NO: 24

The histidine-tagged construct (ht-hTS) consists of the whole sequence of human TS with the MRGSHHHHHHGS sequence added at the N-terminus for a total of 325 amino-acid residues and MW=37114.45 Da. The ht-hTS molecule has a dimeric quaternary structure as indicated by gel-filtration chromatography and confirmed by the crystal structure determination.

The crystals of ht-hTS have been obtained in sitting drop set up from a 200 µM ht-hTS solution in 0.1 M HEPES at pH 7.5 and β-mercaptoethanol 20 mM. 3 µL of the above hTS solution have been mixed with 3 µL of a precipitant solution consisting of 20-25% saturated $(NH_4)_2SO_4$ solution, 20 mM β-mercaptoethanol and 0.1 M Tris-HCl at pH 8.3.

Crystals of the hTS grow in about one week to the final dimensions of about 100×200×200 µm.

Crystals of the ht-hTS complex with the octa-peptide SED ID NO: 24 (LSCQLYQR; ht-hTS-SED ID NO: 24) have been grown in sitting drop set up from the above ht-hTS solution incubated for 2 h at 4° C. with a 1 mM solution of the peptide SED ID NO: 24 in water using the same set up and the same precipitant solution. Crystals of the ht-hTS-SED ID NO: 24 complex appeared in 3-5 days and grew to final dimensions similar to the native crystals in about 3 weeks.

The ht-hTS and ht-hTS-SED ID NO: 24 crystals display the same habit and belong to the trigonal system.

Crystal data have been collected on crystals frozen at 100 K under a cold nitrogen stream upon addition to the crystals mother solution of 20% glycerol as cryoprotectant.

The data collection has been performed at ESRF (Grenoble) on beamlines ID 14-1 and ID 23-1 equipped with ADSC Q210 CCD detectors. The data have been collected by the rotation method using $\Delta\phi=1°$ over 180°, in order to achieve high redundancy, with crystal to detector distance of 265 mm. The crystals were stable on the beam over the data collection time (about 25'), and one crystal was used for each dataset. Final data collection statistics are shown in Table 2.

Structure Solution

The structure of ht-hTS was solved in the trigonal space group $P3_121$ using the molecular replacement technique. The model used was that of a subunit of human TS crystallized in the low salt condition (PDB 1YPV) with all the water molecules omitted.

The asymmetric unit content consists of one subunit of the ht-hTS dimer which occupies a special position of point symmetry 2 with the molecule two-fold axis coincident with a crystallographic two-fold axis present in the cell. The correct orientation and translation of the molecule within the crystallographic unit cell was determined with standard Patterson search techniques, as implemented in the software MOLREP.

The program provided an evident solution for the positioning for the asymmetric unit content. The first 37 N-terminal residues present in the construct were not visible in the electron density map and are not part of our model; residues from 120 to 141 are non visible in the electron density map and are omitted from the model as well as the C-terminus last three residues.

The programs XtalView and Coot have been used for manual rebuilding of the model. The crystal structure of the ht-hTS-SED ID NO: 24 complex has been solved by molecular replacement by using MOLREP and ht-hTS as model. However, the formation of a 1:1 complex between the ht-hTS dimer and the peptide SED ID NO: 24 disrupt the two-fold symmetry of the molecule and lowers the space group symmetry from $P3_121$ to $P3_1$ as later confirmed by the refinement. For ht-hTS-SED ID NO: 24 in $P3_1$, the asymmetric unit content consists of the whole ht-hTS dimer and of the SED ID NO: 24 peptide.

Structure Refinement

The initial models from molecular replacement have been subjected by an initial cycle of rigid body refinement followed by several cycles of conventional maximum-likelihood refinement as implemented in REFMAC5. Between the refinement cycles, the model was subjected to manual rebuild using XtalView and Coot. The program Coot has been used to model the SED ID NO: 24 peptide. Water molecules have been added in all cases by using the standard procedure within the ARP/wARP suite.

The refined model of ht-hTS consists of 263 amino acids, 91 water molecules and 2 sulphate anions from the crystallization solution. Inspection of the Fourier difference maps has shown that four out of the five cysteine residues present in hTS have reacted with β-mercaptoethanol (BME) to give covalent adducts. However, only for Cys211 a whole BME molecule is visible in the electron density map, while for Cys55, Cys192, Cys207 only a sulphur atom is detected and inserted in the model. The tendency of the hTS cysteine residues to react with BME has been previously observed.

The two sulphate anions are bound at the dimer interface by H-bonds to Arg187 and Arg197 in the same anion recognising site where the substrate dUMP binds.

The formation of a 1:1 complex between ht-hTS dimer and the SED ID NO: 24 peptide should vanish the two-fold symmetry present in the enzyme. In order to ascertain if the symmetry of the ht-hTS-SED ID NO: 24 crystal was effectively lowered to $P3_1$, we processed and refined the data in both $P3_121$ and $P3_1$ space groups.

The structure in the space group $P3_121$ was refined by modeling the peptide in two mutually excluding orientations (related by the two-fold axis) and using an occupancy factor of 0.50 for each orientation. On the contrary the peptide occupancy has been kept to 1.00 when performed in $P3_1$ although the refinement ends with high temperature factors (50-70% higher than the hTS atoms) indicating a some what lower occupancy for the SED ID NO: 24 peptide. The final R-cryst and R-free factors converged to of 0.24-0.28 respectively for the structure in $P3_121$ compared to 0.20-0.25 obtained in the space group $P3_1$ when performing the same refinement steps. The lower values of these parameters indicate the correctness of the $P3_1$ space group for the complex.

In the final steps of the refinement ordered water molecules have been added to both ht-hTS and ht-hTS-SED ID NO: 24 structures by the procedure implemented within the ARP/wARP suite.

The stereochemical quality of the refined model was assessed using the program PROCHECK.

TABLE 2

Data collection and refinement statistics.
(The data in parentheses refer to the highest resolution shell)
DATA COLLECTION AND REFINEMENT STATISTICS

|  | ht-hTS | t-hTS-SED ID NO: 24 |
|---|---|---|
| Data collection statistics | | |
| X-ray source | ESRF ID14-1 | ESRF ID23-1 |
| Wavelength (Å) | 0.934 | 0.934 |
| Data coll. Temp. (K) | 100 | 100 |
| Space group | $P3_12$ | $P3_1$ |
| Cell dimensions (Å) | a = 96.20 | a = 96.11 |
|  | b = 96.20 | b = 96.11 |
|  | c = 82.47 | c = 82.24 |
| subunits/asu | 1 | 2 |
| Matthews coeff. ($Å^3Da^{-1}$) | 3.01 | 3.00 |
| Solv. Cont (%) | 59.20 | 59.01 |
| Resolution limits (Å) | 41.67-2.28 (2.40-2.28) | 83.33-2.26 (2.38-2.26) |
| Reflections measured | 219644 (31723) | 438289 (65562) |
| Unique reflections | 20528 (2942) | 39745 (5857) |
| Completeness (%) | 100.0 (100.0) | 99.8 (100.0) |
| $R_{sym}$ (%) | 6.4 (41.3) | 7.1 (30.3) |
| Multiplicity | 10.7 (10.8) | 11.0 (11.2) |
| I/σI | 24.0 (6.6) | 25.9 (6.7) |
| Refinement statistics | | |
| R cryst (%) | 19.6 (22.4) | 20.0 (30.7) |
| R free (%) | 23.6 (26.6) | 25.0 (44.7) |
| Protein atoms | 2130 | 4260 |
| Ligand atoms | 0 | 69 |
| Water molecules | 88 | 261 |
| Average B factor ($Å^2$) | 44.28 | 49.73 |
| r.m.s.d. bond lengths (Å) | 0.023 | 0.032 |
| r.m.s.d. bond angles (°) | 1.974 | 2.450 |

The invention claimed is:

1. A synthetic peptide comprising a peptide selected from the group consisting of SEQ ID NO: 6-7, SEQ ID NO: 9-10, and SEQ ID NO: 103, wherein the synthetic peptide binds at a binding site located in the dimer interface region of thymidylate synthase and has a total length of up to 10 amino acids.

2. The synthetic peptide according to claim 1, wherein the peptide stabilizes thymidylate synthase inactive conformation.

3. The synthetic peptide according to claim 2, wherein the peptide stabilizes thymidylate synthase inactive conformation while retaining thymidylate synthase's mRNA binding ability and related translational repression functions.

4. The synthetic peptide according to claim 1, wherein the thymidylate synthase is human thymidylate synthase.

5. The synthetic peptide according to claim 1, wherein the binding site spans a cleft located at the interface of the two TS subunits defined by loops 149-172 and 183-204 of both A and B subunits.

6. The synthetic peptide according to claim 5, wherein the cleft comprises Cys192 of subunits A and B.

7. The synthetic peptide according to claim 1, wherein the peptide has an inducible secondary structure.

8. A cross-linked synthetic peptide consisting of at least two synthetic peptides according to claim 1, the at least two peptides are bound through at least a covalent bond to give a cross-linked peptide.

9. The synthetic peptide according to claim 1, further comprising an esterified or amidated C-terminal residue, and/or acetylated or alkoxycarbonylamino N-terminal residue, and/or methylated, benzylated, t-butylated, tosylated, or alkoxycarbonylamino amino acid residues.

10. The synthetic peptide according to claim 1, further comprising a residue selected from the group consisting of penicillamine, tetramethylene cysteine, pentamethylene cysteine, mercaptopropionic acid, pentamethylene-mercaptopropionic acid, 2-mercaptobenzene, 2-mercaptoaniline, 2-mercaptoproline, ornithine, diaminobutyric acid, aminoadipic acid, m-aminomethylbenzoic acid, and diaminopropionic acid.

11. The synthetic peptide according to claim 1, wherein the peptide is coupled to a protein transduction (PTDs) or a cell penetrating peptide (CPP).

12. The synthetic peptide according to claim 11, wherein the PTD or CPP is selected from the group consisting of trans-activating transcriptional activator (TAT) peptide, Antennapedia (ANTP) peptide, arginine-rich peptide, and VP22.

13. The synthetic peptide according to claim 1, wherein the peptide is coupled to an antibody, a serum hormone, a lectin, an adhesion molecule, a tumor cell surface binding ligand, a steroid, a cholesterol molecule, a lymphokine, a fibrinolytic enzyme, or a drug or a peptide that binds to a desired target site.

14. A pharmaceutical composition comprising at least one synthetic peptide according to claim 1, together with one or more pharmaceutically acceptable excipients.

15. The pharmaceutical composition according to claim 14, further comprising at least one other anticancer drug.

16. A nucleic acid molecule encoding the synthetic peptide of claim 1.

17. The nucleic acid molecule according to claim 16, wherein the nucleic acid molecule is coupled to viral and non-viral gene delivery vectors.

18. A genetic construct for the expression of a synthetic peptide according to claim 1, comprising a nucleic acid molecule encoding the synthetic peptide.

19. The genetic construct according to claim 18, further comprising one or more regulatory elements selected from the group consisting of a promoter and an enhancer.

20. A synthetic peptide comprising a peptide selected from the group consisting of SEQ ID NO: 5-11, SEQ ID NO: 80, and SEQ ID NO: 103, wherein the synthetic peptide binds at a binding site located in the dimer interface region of thymidylate synthase and has a total length of up to 10 amino acids, and the synthetic peptide is esterified or amidated at the C-terminal residue, and/or acetylated or comprise an alkoxycarbonylamino at the N-terminal residue, and/or having methylated, benzylated, t-butylated, tosylated or alkoxycarbonylamino amino acid residues.

21. A synthetic peptide comprising a peptide selected from the group consisting of SEQ ID NO: 5-11, SEQ ID NO: 80, and SEQ ID NO: 103, wherein the synthetic peptide binds at a binding site located in the dimer interface region of thymidylate synthase and has a total length of up to 10 amino acids, and the synthetic peptide comprises a residue selected from the group consisting of penicillamine, tetramethylene, cysteine, pentamethylene cysteine, mercaptopropionic acid, pentamethylene-mercaptoproionic acid, 2-mercaptobenzene, 2-mercaptoaniline, 2-mercaptoproline, ornithine, diaminobutyric acid, aminoadipic acid, m-aminomethylbenzoic acid, and diaminopropionic acid.

22. The genetic construct according to claim 18, further comprising a selectable marker.

* * * * *

SEQUENCE LISTING

```
<160> NUMBER OF SEQ ID NOS: 186

<210> SEQ ID NO 1
<211> LENGTH: 8
<212> TYPE: PRT
<213> ORGANISM: Artificial
<220> FEATURE:
<223> OTHER INFORMATION: peptide binding to TS

<400> SEQUENCE: 1

Asp Phe Ile His Thr Leu Gly Asp
1               5
```

```
<210> SEQ ID NO 2
<211> LENGTH: 8
<212> TYPE: PRT
<213> ORGANISM: Artificial
<220> FEATURE:
<223> OTHER INFORMATION: peptide binding to TS
<220> FEATURE:
<221> NAME/KEY: MOD_RES
<222> LOCATION: (1)..(1)
<223> OTHER INFORMATION: ACETYLATION

<400> SEQUENCE: 2

Asp Phe Ile His Thr Leu Gly Asp
1               5

<210> SEQ ID NO 3
<211> LENGTH: 8
<212> TYPE: PRT
<213> ORGANISM: Artificial
<220> FEATURE:
<223> OTHER INFORMATION: peptide binding to TS
<220> FEATURE:
<221> NAME/KEY: MOD_RES
<222> LOCATION: (8)..(8)
<223> OTHER INFORMATION: AMIDATION

<400> SEQUENCE: 3

Asp Phe Ile His Thr Leu Gly Asp
1               5

<210> SEQ ID NO 4
<211> LENGTH: 8
<212> TYPE: PRT
<213> ORGANISM: Artificial
<220> FEATURE:
<223> OTHER INFORMATION: peptide binding to TS
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (8)..(8)
<223> OTHER INFORMATION: AMIDATION

<400> SEQUENCE: 4

Asp Phe Ile His Thr Leu Gly Asp
1               5

<210> SEQ ID NO 5
<211> LENGTH: 8
<212> TYPE: PRT
<213> ORGANISM: Artificial
<220> FEATURE:
<223> OTHER INFORMATION: peptide binding to TS

<400> SEQUENCE: 5

Ala Phe Ile His Thr Leu Gly Asp
1               5

<210> SEQ ID NO 6
<211> LENGTH: 8
<212> TYPE: PRT
<213> ORGANISM: Artificial
<220> FEATURE:
<223> OTHER INFORMATION: peptide binding to TS

<400> SEQUENCE: 6
```

```
Asp Ala Ile His Thr Leu Gly Asp
1               5

<210> SEQ ID NO 7
<211> LENGTH: 8
<212> TYPE: PRT
<213> ORGANISM: Artificial
<220> FEATURE:
<223> OTHER INFORMATION: peptide binding to TS

<400> SEQUENCE: 7

Asp Phe Ala His Thr Leu Gly Asp
1               5

<210> SEQ ID NO 8
<211> LENGTH: 8
<212> TYPE: PRT
<213> ORGANISM: Artificial
<220> FEATURE:
<223> OTHER INFORMATION: peptide binding to TS

<400> SEQUENCE: 8

Asp Phe Ile Ala Thr Leu Gly Asp
1               5

<210> SEQ ID NO 9
<211> LENGTH: 8
<212> TYPE: PRT
<213> ORGANISM: Artificial
<220> FEATURE:
<223> OTHER INFORMATION: peptide binding to TS

<400> SEQUENCE: 9

Asp Phe Ile His Ala Leu Gly Asp
1               5

<210> SEQ ID NO 10
<211> LENGTH: 8
<212> TYPE: PRT
<213> ORGANISM: Artificial
<220> FEATURE:
<223> OTHER INFORMATION: peptide binding to TS

<400> SEQUENCE: 10

Asp Phe Ile His Thr Ala Gly Asp
1               5

<210> SEQ ID NO 11
<211> LENGTH: 8
<212> TYPE: PRT
<213> ORGANISM: Artificial
<220> FEATURE:
<223> OTHER INFORMATION: peptide binding to TS

<400> SEQUENCE: 11

Asp Phe Ile His Thr Leu Ala Asp
1               5

<210> SEQ ID NO 12
<211> LENGTH: 8
<212> TYPE: PRT
<213> ORGANISM: Artificial
<220> FEATURE:
<223> OTHER INFORMATION: peptide binding to TS

<400> SEQUENCE: 12

Asp Phe Ile His Thr Leu Gly Ala
```

```
1               5

<210> SEQ ID NO 13
<211> LENGTH: 7
<212> TYPE: PRT
<213> ORGANISM: Artificial
<220> FEATURE:
<223> OTHER INFORMATION: peptide binding to TS

<400> SEQUENCE: 13

Phe Ile His Thr Leu Gly Asp
1               5

<210> SEQ ID NO 14
<211> LENGTH: 6
<212> TYPE: PRT
<213> ORGANISM: Artificial
<220> FEATURE:
<223> OTHER INFORMATION: peptide binding to TS

<400> SEQUENCE: 14

Ile His Thr Leu Gly Asp
1               5

<210> SEQ ID NO 15
<211> LENGTH: 5
<212> TYPE: PRT
<213> ORGANISM: Artificial
<220> FEATURE:
<223> OTHER INFORMATION: peptide binding to TS

<400> SEQUENCE: 15

His Thr Leu Gly Asp
1               5

<210> SEQ ID NO 16
<211> LENGTH: 7
<212> TYPE: PRT
<213> ORGANISM: Artificial
<220> FEATURE:
<223> OTHER INFORMATION: peptide binding to TS

<400> SEQUENCE: 16

Asp Phe Ile His Thr Leu Gly
1               5

<210> SEQ ID NO 17
<211> LENGTH: 6
<212> TYPE: PRT
<213> ORGANISM: Artificial
<220> FEATURE:
<223> OTHER INFORMATION: peptide binding to TS

<400> SEQUENCE: 17

Asp Phe Ile His Thr Leu
1               5

<210> SEQ ID NO 18
<211> LENGTH: 5
<212> TYPE: PRT
<213> ORGANISM: Artificial
<220> FEATURE:
<223> OTHER INFORMATION: peptide binding to TS

<400> SEQUENCE: 18

Asp Phe Ile His Thr
1               5
```

```
<210> SEQ ID NO 19
<211> LENGTH: 5
<212> TYPE: PRT
<213> ORGANISM: Artificial
<220> FEATURE:
<223> OTHER INFORMATION: peptide binding to TS

<400> SEQUENCE: 19

Phe Ile His Thr Leu
1               5

<210> SEQ ID NO 20
<211> LENGTH: 5
<212> TYPE: PRT
<213> ORGANISM: Artificial
<220> FEATURE:
<223> OTHER INFORMATION: peptide binding to TS

<400> SEQUENCE: 20

Ile His Thr Leu Gly
1               5

<210> SEQ ID NO 21
<211> LENGTH: 8
<212> TYPE: PRT
<213> ORGANISM: Artificial
<220> FEATURE:
<223> OTHER INFORMATION: peptide binding to TS

<400> SEQUENCE: 21

Leu Lys Tyr Val Trp Asn Pro Leu
1               5

<210> SEQ ID NO 22
<211> LENGTH: 8
<212> TYPE: PRT
<213> ORGANISM: Artificial
<220> FEATURE:
<223> OTHER INFORMATION: peptide binding to TS

<400> SEQUENCE: 22

Leu Lys Tyr Val Cys Asn Pro Leu
1               5

<210> SEQ ID NO 23
<211> LENGTH: 8
<212> TYPE: PRT
<213> ORGANISM: Artificial
<220> FEATURE:
<223> OTHER INFORMATION: peptide binding to TS

<400> SEQUENCE: 23

Val Lys Tyr Val Ser Gln Ser Ile
1               5

<210> SEQ ID NO 24
<211> LENGTH: 8
<212> TYPE: PRT
<213> ORGANISM: Artificial
<220> FEATURE:
<223> OTHER INFORMATION: peptide binding to TS

<400> SEQUENCE: 24

Leu Ser Cys Gln Leu Tyr Gln Arg
1               5
```

```
<210> SEQ ID NO 25
<211> LENGTH: 8
<212> TYPE: PRT
<213> ORGANISM: Artificial
<220> FEATURE:
<223> OTHER INFORMATION: peptide binding to TS

<400> SEQUENCE: 25

Ala Ser Cys Gln Leu Tyr Gln Arg
1               5

<210> SEQ ID NO 26
<211> LENGTH: 8
<212> TYPE: PRT
<213> ORGANISM: Artificial
<220> FEATURE:
<223> OTHER INFORMATION: peptide binding to TS

<400> SEQUENCE: 26

Leu Ala Cys Gln Leu Tyr Gln Arg
1               5

<210> SEQ ID NO 27
<211> LENGTH: 8
<212> TYPE: PRT
<213> ORGANISM: Artificial
<220> FEATURE:
<223> OTHER INFORMATION: peptide binding to TS

<400> SEQUENCE: 27

Leu Ser Ala Gln Leu Tyr Gln Arg
1               5

<210> SEQ ID NO 28
<211> LENGTH: 8
<212> TYPE: PRT
<213> ORGANISM: Artificial
<220> FEATURE:
<223> OTHER INFORMATION: peptide binding to TS

<400> SEQUENCE: 28

Leu Ser Cys Ala Leu Tyr Gln Arg
1               5

<210> SEQ ID NO 29
<211> LENGTH: 8
<212> TYPE: PRT
<213> ORGANISM: Artificial
<220> FEATURE:
<223> OTHER INFORMATION: peptide binding to TS

<400> SEQUENCE: 29

Leu Ser Cys Gln Ala Tyr Gln Arg
1               5

<210> SEQ ID NO 30
<211> LENGTH: 8
<212> TYPE: PRT
<213> ORGANISM: Artificial
<220> FEATURE:
<223> OTHER INFORMATION: peptide binding to TS

<400> SEQUENCE: 30

Leu Ser Cys Gln Leu Ala Gln Arg
1               5
```

```
<210> SEQ ID NO 31
<211> LENGTH: 8
<212> TYPE: PRT
<213> ORGANISM: Artificial
<220> FEATURE:
<223> OTHER INFORMATION: peptide binding to TS

<400> SEQUENCE: 31

Leu Ser Cys Gln Leu Tyr Ala Arg
1               5

<210> SEQ ID NO 32
<211> LENGTH: 8
<212> TYPE: PRT
<213> ORGANISM: Artificial
<220> FEATURE:
<223> OTHER INFORMATION: peptide binding to TS

<400> SEQUENCE: 32

Leu Ser Cys Gln Leu Tyr Gln Ala
1               5

<210> SEQ ID NO 33
<211> LENGTH: 7
<212> TYPE: PRT
<213> ORGANISM: Artificial
<220> FEATURE:
<223> OTHER INFORMATION: peptide binding to TS

<400> SEQUENCE: 33

Ser Cys Gln Leu Tyr Gln Arg
1               5

<210> SEQ ID NO 34
<211> LENGTH: 6
<212> TYPE: PRT
<213> ORGANISM: Artificial
<220> FEATURE:
<223> OTHER INFORMATION: peptide binding to TS

<400> SEQUENCE: 34

Cys Gln Leu Tyr Gln Arg
1               5

<210> SEQ ID NO 35
<211> LENGTH: 5
<212> TYPE: PRT
<213> ORGANISM: Artificial
<220> FEATURE:
<223> OTHER INFORMATION: peptide binding to TS

<400> SEQUENCE: 35

Gln Leu Tyr Gln Arg
1               5

<210> SEQ ID NO 36
<211> LENGTH: 7
<212> TYPE: PRT
<213> ORGANISM: Artificial
<220> FEATURE:
<223> OTHER INFORMATION: peptide binding to TS

<400> SEQUENCE: 36

Leu Ser Cys Gln Leu Tyr Gln
1               5

<210> SEQ ID NO 37
```

```
<211> LENGTH: 6
<212> TYPE: PRT
<213> ORGANISM: Artificial
<220> FEATURE:
<223> OTHER INFORMATION: peptide binding to TS

<400> SEQUENCE: 37

Leu Ser Cys Gln Leu Tyr
1               5

<210> SEQ ID NO 38
<211> LENGTH: 5
<212> TYPE: PRT
<213> ORGANISM: Artificial
<220> FEATURE:
<223> OTHER INFORMATION: peptide binding to TS

<400> SEQUENCE: 38

Leu Ser Cys Gln Leu
1               5

<210> SEQ ID NO 39
<211> LENGTH: 5
<212> TYPE: PRT
<213> ORGANISM: Artificial
<220> FEATURE:
<223> OTHER INFORMATION: peptide binding to TS

<400> SEQUENCE: 39

Ser Cys Gln Leu Tyr
1               5

<210> SEQ ID NO 40
<211> LENGTH: 5
<212> TYPE: PRT
<213> ORGANISM: Artificial
<220> FEATURE:
<223> OTHER INFORMATION: peptide binding to TS

<400> SEQUENCE: 40

Cys Gln Leu Tyr Gln
1               5

<210> SEQ ID NO 41
<211> LENGTH: 8
<212> TYPE: PRT
<213> ORGANISM: Artificial
<220> FEATURE:
<223> OTHER INFORMATION: peptide binding to TS

<400> SEQUENCE: 41

Leu Ser Ser Gln Leu Tyr Gln Arg
1               5

<210> SEQ ID NO 42
<211> LENGTH: 8
<212> TYPE: PRT
<213> ORGANISM: Artificial
<220> FEATURE:
<223> OTHER INFORMATION: peptide binding to TS

<400> SEQUENCE: 42

Asp Arg Thr Val Asp Met Val Ser
1               5

<210> SEQ ID NO 43
<211> LENGTH: 8
```

```
<212> TYPE: PRT
<213> ORGANISM: Artificial
<220> FEATURE:
<223> OTHER INFORMATION: peptide binding to TS

<400> SEQUENCE: 43

Gln Gly Ala Leu Gln Val Leu Ser
1               5

<210> SEQ ID NO 44
<211> LENGTH: 8
<212> TYPE: PRT
<213> ORGANISM: Artificial
<220> FEATURE:
<223> OTHER INFORMATION: peptide binding to TS

<400> SEQUENCE: 44

Tyr Val Val Asn Ser Glu Leu Ser
1               5

<210> SEQ ID NO 45
<211> LENGTH: 8
<212> TYPE: PRT
<213> ORGANISM: Artificial
<220> FEATURE:
<223> OTHER INFORMATION: peptide binding to TS

<400> SEQUENCE: 45

Ala Val Val Asn Ser Glu Leu Ser
1               5

<210> SEQ ID NO 46
<211> LENGTH: 8
<212> TYPE: PRT
<213> ORGANISM: Artificial
<220> FEATURE:
<223> OTHER INFORMATION: peptide binding to TS

<400> SEQUENCE: 46

Tyr Ala Val Asn Ser Glu Leu Ser
1               5

<210> SEQ ID NO 47
<211> LENGTH: 8
<212> TYPE: PRT
<213> ORGANISM: Artificial
<220> FEATURE:
<223> OTHER INFORMATION: peptide binding to TS

<400> SEQUENCE: 47

Tyr Val Ala Asn Ser Glu Leu Ser
1               5

<210> SEQ ID NO 48
<211> LENGTH: 8
<212> TYPE: PRT
<213> ORGANISM: Artificial
<220> FEATURE:
<223> OTHER INFORMATION: peptide binding to TS

<400> SEQUENCE: 48

Tyr Val Val Ala Ser Glu Leu Ser
1               5

<210> SEQ ID NO 49
<211> LENGTH: 8
<212> TYPE: PRT
```

```
<213> ORGANISM: Artificial
<220> FEATURE:
<223> OTHER INFORMATION: peptide binding to TS

<400> SEQUENCE: 49

Tyr Val Val Asn Ala Glu Leu Ser
1               5

<210> SEQ ID NO 50
<211> LENGTH: 8
<212> TYPE: PRT
<213> ORGANISM: Artificial
<220> FEATURE:
<223> OTHER INFORMATION: peptide binding to TS

<400> SEQUENCE: 50

Tyr Val Val Asn Ser Ala Leu Ser
1               5

<210> SEQ ID NO 51
<211> LENGTH: 8
<212> TYPE: PRT
<213> ORGANISM: Artificial
<220> FEATURE:
<223> OTHER INFORMATION: peptide binding to TS

<400> SEQUENCE: 51

Tyr Val Val Asn Ser Glu Ala Ser
1               5

<210> SEQ ID NO 52
<211> LENGTH: 8
<212> TYPE: PRT
<213> ORGANISM: Artificial
<220> FEATURE:
<223> OTHER INFORMATION: peptide binding to TS

<400> SEQUENCE: 52

Tyr Val Val Asn Ser Glu Leu Ala
1               5

<210> SEQ ID NO 53
<211> LENGTH: 7
<212> TYPE: PRT
<213> ORGANISM: Artificial
<220> FEATURE:
<223> OTHER INFORMATION: peptide binding to TS

<400> SEQUENCE: 53

Val Val Asn Ser Glu Leu Ser
1               5

<210> SEQ ID NO 54
<211> LENGTH: 6
<212> TYPE: PRT
<213> ORGANISM: Artificial
<220> FEATURE:
<223> OTHER INFORMATION: peptide binding to TS

<400> SEQUENCE: 54

Val Asn Ser Glu Leu Ser
1               5

<210> SEQ ID NO 55
<211> LENGTH: 5
<212> TYPE: PRT
<213> ORGANISM: Artificial
```

```
<220> FEATURE:
<223> OTHER INFORMATION: peptide binding to TS

<400> SEQUENCE: 55

Asn Ser Glu Leu Ser
1               5

<210> SEQ ID NO 56
<211> LENGTH: 7
<212> TYPE: PRT
<213> ORGANISM: Artificial
<220> FEATURE:
<223> OTHER INFORMATION: peptide binding to TS

<400> SEQUENCE: 56

Tyr Val Val Asn Ser Glu Leu
1               5

<210> SEQ ID NO 57
<211> LENGTH: 6
<212> TYPE: PRT
<213> ORGANISM: Artificial
<220> FEATURE:
<223> OTHER INFORMATION: peptide binding to TS

<400> SEQUENCE: 57

Tyr Val Val Asn Ser Glu
1               5

<210> SEQ ID NO 58
<211> LENGTH: 5
<212> TYPE: PRT
<213> ORGANISM: Artificial
<220> FEATURE:
<223> OTHER INFORMATION: peptide binding to TS

<400> SEQUENCE: 58

Tyr Val Val Asn Ser
1               5

<210> SEQ ID NO 59
<211> LENGTH: 5
<212> TYPE: PRT
<213> ORGANISM: Artificial
<220> FEATURE:
<223> OTHER INFORMATION: peptide binding to TS

<400> SEQUENCE: 59

Val Val Asn Ser Glu
1               5

<210> SEQ ID NO 60
<211> LENGTH: 5
<212> TYPE: PRT
<213> ORGANISM: Artificial
<220> FEATURE:
<223> OTHER INFORMATION: peptide binding to TS

<400> SEQUENCE: 60

Val Asn Ser Glu Leu
1               5

<210> SEQ ID NO 61
<211> LENGTH: 8
<212> TYPE: PRT
<213> ORGANISM: Artificial
<220> FEATURE:
```

```
<223> OTHER INFORMATION: peptide binding to TS

<400> SEQUENCE: 61

Ile His His Leu Ser Leu Asp Arg
1               5

<210> SEQ ID NO 62
<211> LENGTH: 8
<212> TYPE: PRT
<213> ORGANISM: Artificial
<220> FEATURE:
<223> OTHER INFORMATION: peptide binding to TS

<400> SEQUENCE: 62

Ile His His Val Thr Leu Gln Gly
1               5

<210> SEQ ID NO 63
<211> LENGTH: 8
<212> TYPE: PRT
<213> ORGANISM: Artificial
<220> FEATURE:
<223> OTHER INFORMATION: peptide binding to TS

<400> SEQUENCE: 63

Cys Gln Leu Tyr Gln Arg Ser Gly
1               5

<210> SEQ ID NO 64
<211> LENGTH: 8
<212> TYPE: PRT
<213> ORGANISM: Artificial
<220> FEATURE:
<223> OTHER INFORMATION: peptide binding to TS

<400> SEQUENCE: 64

Ala Gln Leu Tyr Gln Arg Ser Gly
1               5

<210> SEQ ID NO 65
<211> LENGTH: 8
<212> TYPE: PRT
<213> ORGANISM: Artificial
<220> FEATURE:
<223> OTHER INFORMATION: peptide binding to TS

<400> SEQUENCE: 65

Cys Ala Leu Tyr Gln Arg Ser Gly
1               5

<210> SEQ ID NO 66
<211> LENGTH: 8
<212> TYPE: PRT
<213> ORGANISM: Artificial
<220> FEATURE:
<223> OTHER INFORMATION: peptide binding to TS

<400> SEQUENCE: 66

Cys Gln Ala Tyr Gln Arg Ser Gly
1               5

<210> SEQ ID NO 67
<211> LENGTH: 8
<212> TYPE: PRT
<213> ORGANISM: Artificial
<220> FEATURE:
<223> OTHER INFORMATION: peptide binding to TS
```

<400> SEQUENCE: 67

Cys Gln Leu Ala Gln Arg Ser Gly
1               5

<210> SEQ ID NO 68
<211> LENGTH: 8
<212> TYPE: PRT
<213> ORGANISM: Artificial
<220> FEATURE:
<223> OTHER INFORMATION: peptide binding to TS

<400> SEQUENCE: 68

Cys Gln Leu Tyr Ala Arg Ser Gly
1               5

<210> SEQ ID NO 69
<211> LENGTH: 8
<212> TYPE: PRT
<213> ORGANISM: Artificial
<220> FEATURE:
<223> OTHER INFORMATION: peptide binding to TS

<400> SEQUENCE: 69

Cys Gln Leu Tyr Gln Ala Ser Gly
1               5

<210> SEQ ID NO 70
<211> LENGTH: 8
<212> TYPE: PRT
<213> ORGANISM: Artificial
<220> FEATURE:
<223> OTHER INFORMATION: peptide binding to TS

<400> SEQUENCE: 70

Cys Gln Leu Tyr Gln Arg Ala Gly
1               5

<210> SEQ ID NO 71
<211> LENGTH: 8
<212> TYPE: PRT
<213> ORGANISM: Artificial
<220> FEATURE:
<223> OTHER INFORMATION: peptide binding to TS

<400> SEQUENCE: 71

Cys Gln Leu Tyr Gln Arg Ser Ala
1               5

<210> SEQ ID NO 72
<211> LENGTH: 7
<212> TYPE: PRT
<213> ORGANISM: Artificial
<220> FEATURE:
<223> OTHER INFORMATION: peptide binding to TS

<400> SEQUENCE: 72

Gln Leu Tyr Gln Arg Ser Gly
1               5

<210> SEQ ID NO 73
<211> LENGTH: 6
<212> TYPE: PRT
<213> ORGANISM: Artificial
<220> FEATURE:
<223> OTHER INFORMATION: peptide binding to TS

```
<400> SEQUENCE: 73

Leu Tyr Gln Arg Ser Gly
1               5

<210> SEQ ID NO 74
<211> LENGTH: 5
<212> TYPE: PRT
<213> ORGANISM: Artificial
<220> FEATURE:
<223> OTHER INFORMATION: peptide binding to TS

<400> SEQUENCE: 74

Tyr Gln Arg Ser Gly
1               5

<210> SEQ ID NO 75
<211> LENGTH: 7
<212> TYPE: PRT
<213> ORGANISM: Artificial
<220> FEATURE:
<223> OTHER INFORMATION: peptide binding to TS

<400> SEQUENCE: 75

Cys Gln Leu Tyr Gln Arg Ser
1               5

<210> SEQ ID NO 76
<211> LENGTH: 6
<212> TYPE: PRT
<213> ORGANISM: Artificial
<220> FEATURE:
<223> OTHER INFORMATION: peptide binding to TS

<400> SEQUENCE: 76

Cys Gln Leu Tyr Gln Arg
1               5

<210> SEQ ID NO 77
<211> LENGTH: 5
<212> TYPE: PRT
<213> ORGANISM: Artificial
<220> FEATURE:
<223> OTHER INFORMATION: peptide binding to TS

<400> SEQUENCE: 77

Cys Gln Leu Tyr Gln
1               5

<210> SEQ ID NO 78
<211> LENGTH: 5
<212> TYPE: PRT
<213> ORGANISM: Artificial
<220> FEATURE:
<223> OTHER INFORMATION: peptide binding to TS

<400> SEQUENCE: 78

Gln Leu Tyr Gln Arg
1               5

<210> SEQ ID NO 79
<211> LENGTH: 5
<212> TYPE: PRT
<213> ORGANISM: Artificial
<220> FEATURE:
<223> OTHER INFORMATION: peptide binding to TS

<400> SEQUENCE: 79
```

```
Leu Tyr Gln Arg Ser
1               5

<210> SEQ ID NO 80
<211> LENGTH: 8
<212> TYPE: PRT
<213> ORGANISM: Artificial
<220> FEATURE:
<223> OTHER INFORMATION: peptide binding to TS

<400> SEQUENCE: 80

Ser Gln Leu Tyr Gln Arg Ser Gly
1               5

<210> SEQ ID NO 81
<211> LENGTH: 8
<212> TYPE: PRT
<213> ORGANISM: Artificial
<220> FEATURE:
<223> OTHER INFORMATION: peptide binding to TS

<400> SEQUENCE: 81

Thr Val Asp Met Val Ser Ser Pro
1               5

<210> SEQ ID NO 82
<211> LENGTH: 8
<212> TYPE: PRT
<213> ORGANISM: Artificial
<220> FEATURE:
<223> OTHER INFORMATION: peptide binding to TS

<400> SEQUENCE: 82

Ala Leu Gln Val Leu Ser Arg Ser
1               5

<210> SEQ ID NO 83
<211> LENGTH: 8
<212> TYPE: PRT
<213> ORGANISM: Artificial
<220> FEATURE:
<223> OTHER INFORMATION: peptide binding to TS

<400> SEQUENCE: 83

Gln Phe Tyr Val Val Asn Ser Glu
1               5

<210> SEQ ID NO 84
<211> LENGTH: 8
<212> TYPE: PRT
<213> ORGANISM: Artificial
<220> FEATURE:
<223> OTHER INFORMATION: peptide binding to TS

<400> SEQUENCE: 84

Val Asn Ser Glu Leu Ser Cys Gln
1               5

<210> SEQ ID NO 85
<211> LENGTH: 8
<212> TYPE: PRT
<213> ORGANISM: Artificial
<220> FEATURE:
<223> OTHER INFORMATION: peptide binding to TS

<400> SEQUENCE: 85
```

```
Ser Glu Leu Ser Cys Gln Leu Tyr
1               5

<210> SEQ ID NO 86
<211> LENGTH: 8
<212> TYPE: PRT
<213> ORGANISM: Artificial
<220> FEATURE:
<223> OTHER INFORMATION: peptide binding to TS

<400> SEQUENCE: 86

Leu Cys Gln Phe Tyr Val Val Asn
1               5

<210> SEQ ID NO 87
<211> LENGTH: 8
<212> TYPE: PRT
<213> ORGANISM: Artificial
<220> FEATURE:
<223> OTHER INFORMATION: peptide binding to TS

<400> SEQUENCE: 87

Ala Cys Gln Phe Tyr Val Val Asn
1               5

<210> SEQ ID NO 88
<211> LENGTH: 8
<212> TYPE: PRT
<213> ORGANISM: Artificial
<220> FEATURE:
<223> OTHER INFORMATION: peptide binding to TS

<400> SEQUENCE: 88

Leu Ala Gln Phe Tyr Val Val Asn
1               5

<210> SEQ ID NO 89
<211> LENGTH: 8
<212> TYPE: PRT
<213> ORGANISM: Artificial
<220> FEATURE:
<223> OTHER INFORMATION: peptide binding to TS

<400> SEQUENCE: 89

Leu Cys Ala Phe Tyr Val Val Asn
1               5

<210> SEQ ID NO 90
<211> LENGTH: 8
<212> TYPE: PRT
<213> ORGANISM: Artificial
<220> FEATURE:
<223> OTHER INFORMATION: peptide binding to TS

<400> SEQUENCE: 90

Leu Cys Gln Ala Tyr Val Val Asn
1               5

<210> SEQ ID NO 91
<211> LENGTH: 8
<212> TYPE: PRT
<213> ORGANISM: Artificial
<220> FEATURE:
<223> OTHER INFORMATION: peptide binding to TS

<400> SEQUENCE: 91

Leu Cys Gln Phe Ala Val Val Asn
```

```
1               5

<210> SEQ ID NO 92
<211> LENGTH: 8
<212> TYPE: PRT
<213> ORGANISM: Artificial
<220> FEATURE:
<223> OTHER INFORMATION: peptide binding to TS

<400> SEQUENCE: 92

Leu Cys Gln Phe Tyr Ala Val Asn
1               5

<210> SEQ ID NO 93
<211> LENGTH: 8
<212> TYPE: PRT
<213> ORGANISM: Artificial
<220> FEATURE:
<223> OTHER INFORMATION: peptide binding to TS

<400> SEQUENCE: 93

Leu Cys Gln Phe Tyr Val Ala Asn
1               5

<210> SEQ ID NO 94
<211> LENGTH: 8
<212> TYPE: PRT
<213> ORGANISM: Artificial
<220> FEATURE:
<223> OTHER INFORMATION: peptide binding to TS

<400> SEQUENCE: 94

Leu Cys Gln Phe Tyr Val Val Ala
1               5

<210> SEQ ID NO 95
<211> LENGTH: 7
<212> TYPE: PRT
<213> ORGANISM: Artificial
<220> FEATURE:
<223> OTHER INFORMATION: peptide binding to TS

<400> SEQUENCE: 95

Cys Gln Phe Tyr Val Val Asn
1               5

<210> SEQ ID NO 96
<211> LENGTH: 6
<212> TYPE: PRT
<213> ORGANISM: Artificial
<220> FEATURE:
<223> OTHER INFORMATION: peptide binding to TS

<400> SEQUENCE: 96

Gln Phe Tyr Val Val Asn
1               5

<210> SEQ ID NO 97
<211> LENGTH: 5
<212> TYPE: PRT
<213> ORGANISM: Artificial
<220> FEATURE:
<223> OTHER INFORMATION: peptide binding to TS

<400> SEQUENCE: 97

Phe Tyr Val Val Asn
1               5
```

```
<210> SEQ ID NO 98
<211> LENGTH: 7
<212> TYPE: PRT
<213> ORGANISM: Artificial
<220> FEATURE:
<223> OTHER INFORMATION: peptide binding to TS

<400> SEQUENCE: 98

Leu Cys Gln Phe Tyr Val Val
1               5

<210> SEQ ID NO 99
<211> LENGTH: 6
<212> TYPE: PRT
<213> ORGANISM: Artificial
<220> FEATURE:
<223> OTHER INFORMATION: peptide binding to TS

<400> SEQUENCE: 99

Leu Cys Gln Phe Tyr Val
1               5

<210> SEQ ID NO 100
<211> LENGTH: 5
<212> TYPE: PRT
<213> ORGANISM: Artificial
<220> FEATURE:
<223> OTHER INFORMATION: peptide binding to TS

<400> SEQUENCE: 100

Leu Cys Gln Phe Tyr
1               5

<210> SEQ ID NO 101
<211> LENGTH: 5
<212> TYPE: PRT
<213> ORGANISM: Artificial
<220> FEATURE:
<223> OTHER INFORMATION: peptide binding to TS

<400> SEQUENCE: 101

Cys Gln Phe Tyr Val
1               5

<210> SEQ ID NO 102
<211> LENGTH: 5
<212> TYPE: PRT
<213> ORGANISM: Artificial
<220> FEATURE:
<223> OTHER INFORMATION: peptide binding to TS

<400> SEQUENCE: 102

Gln Phe Tyr Val Val
1               5

<210> SEQ ID NO 103
<211> LENGTH: 8
<212> TYPE: PRT
<213> ORGANISM: Artificial
<220> FEATURE:
<223> OTHER INFORMATION: peptide binding to TS

<400> SEQUENCE: 103

Leu Ser Gln Phe Tyr Val Val Asn
1               5
```

<210> SEQ ID NO 104
<211> LENGTH: 8
<212> TYPE: PRT
<213> ORGANISM: Artificial
<220> FEATURE:
<223> OTHER INFORMATION: peptide binding to TS

<400> SEQUENCE: 104

Glu Thr Val Lys Ile His His Leu
1               5

<210> SEQ ID NO 105
<211> LENGTH: 8
<212> TYPE: PRT
<213> ORGANISM: Artificial
<220> FEATURE:
<223> OTHER INFORMATION: peptide binding to TS

<400> SEQUENCE: 105

Glu Ala Leu Glu Ile His His Val
1               5

<210> SEQ ID NO 106
<211> LENGTH: 5
<212> TYPE: PRT
<213> ORGANISM: Artificial
<220> FEATURE:
<223> OTHER INFORMATION: peptide binding to TS

<400> SEQUENCE: 106

Pro Pro Cys His Ala
1               5

<210> SEQ ID NO 107
<211> LENGTH: 5
<212> TYPE: PRT
<213> ORGANISM: Artificial
<220> FEATURE:
<223> OTHER INFORMATION: peptide binding to TS

<400> SEQUENCE: 107

Pro Pro Ser His Ala
1               5

<210> SEQ ID NO 108
<211> LENGTH: 5
<212> TYPE: PRT
<213> ORGANISM: Artificial
<220> FEATURE:
<223> OTHER INFORMATION: peptide binding to TS

<400> SEQUENCE: 108

Gly Gly Thr Val Arg
1               5

<210> SEQ ID NO 109
<211> LENGTH: 5
<212> TYPE: PRT
<213> ORGANISM: Artificial
<220> FEATURE:
<223> OTHER INFORMATION: peptide binding to TS

<400> SEQUENCE: 109

Arg Trp Ala Met Gly
1               5

```
<210> SEQ ID NO 110
<211> LENGTH: 8
<212> TYPE: PRT
<213> ORGANISM: Artificial
<220> FEATURE:
<223> OTHER INFORMATION: peptide binding to TS

<400> SEQUENCE: 110

Asp Asp Arg Thr Gly Thr Gly Thr
1               5

<210> SEQ ID NO 111
<211> LENGTH: 8
<212> TYPE: PRT
<213> ORGANISM: Artificial
<220> FEATURE:
<223> OTHER INFORMATION: peptide bindingt o TS

<400> SEQUENCE: 111

Leu Leu Ala Cys Pro Trp Pro Trp
1               5

<210> SEQ ID NO 112
<211> LENGTH: 8
<212> TYPE: PRT
<213> ORGANISM: Artificial
<220> FEATURE:
<223> OTHER INFORMATION: peptide binding to TS

<400> SEQUENCE: 112

Val Val Ala Arg Ala Gly Ala Gly
1               5

<210> SEQ ID NO 113
<211> LENGTH: 3
<212> TYPE: PRT
<213> ORGANISM: Artificial
<220> FEATURE:
<223> OTHER INFORMATION: peptide binding to TS

<400> SEQUENCE: 113

Val Asp Gln
1

<210> SEQ ID NO 114
<211> LENGTH: 3
<212> TYPE: PRT
<213> ORGANISM: Artificial
<220> FEATURE:
<223> OTHER INFORMATION: peptide binding to TS

<400> SEQUENCE: 114

Gln Leu Val
1

<210> SEQ ID NO 115
<211> LENGTH: 3
<212> TYPE: PRT
<213> ORGANISM: Artificial
<220> FEATURE:
<223> OTHER INFORMATION: peptide binding to TS

<400> SEQUENCE: 115

Asn Val Leu
1

<210> SEQ ID NO 116
```

```
<211> LENGTH: 3
<212> TYPE: PRT
<213> ORGANISM: Artificial
<220> FEATURE:
<223> OTHER INFORMATION: peptide binding to TS

<400> SEQUENCE: 116

Asp Asp Arg
1

<210> SEQ ID NO 117
<211> LENGTH: 3
<212> TYPE: PRT
<213> ORGANISM: Artificial
<220> FEATURE:
<223> OTHER INFORMATION: peptide binding to TS

<400> SEQUENCE: 117

Leu Leu Ser
1

<210> SEQ ID NO 118
<211> LENGTH: 3
<212> TYPE: PRT
<213> ORGANISM: Artificial
<220> FEATURE:
<223> OTHER INFORMATION: peptide binding to TS

<400> SEQUENCE: 118

Val Val Ser
1

<210> SEQ ID NO 119
<211> LENGTH: 5
<212> TYPE: PRT
<213> ORGANISM: Artificial
<220> FEATURE:
<223> OTHER INFORMATION: peptide binding to TS

<400> SEQUENCE: 119

Arg Ile Ile Met Cys
1               5

<210> SEQ ID NO 120
<211> LENGTH: 5
<212> TYPE: PRT
<213> ORGANISM: Artificial
<220> FEATURE:
<223> OTHER INFORMATION: peptide binding to TS

<400> SEQUENCE: 120

Arg Ile Ile Met Ser
1               5

<210> SEQ ID NO 121
<211> LENGTH: 5
<212> TYPE: PRT
<213> ORGANISM: Artificial
<220> FEATURE:
<223> OTHER INFORMATION: peptide binding to TS

<400> SEQUENCE: 121

Ser Tyr Tyr Tyr Thr
1               5

<210> SEQ ID NO 122
<211> LENGTH: 5
```

```
<212> TYPE: PRT
<213> ORGANISM: Artificial
<220> FEATURE:
<223> OTHER INFORMATION: peptide binding to TS

<400> SEQUENCE: 122

Ser Asp Asp His Ala
1               5

<210> SEQ ID NO 123
<211> LENGTH: 3
<212> TYPE: PRT
<213> ORGANISM: Artificial
<220> FEATURE:
<223> OTHER INFORMATION: peptide binding to TS

<400> SEQUENCE: 123

Val Arg Lys
1

<210> SEQ ID NO 124
<211> LENGTH: 3
<212> TYPE: PRT
<213> ORGANISM: Artificial
<220> FEATURE:
<223> OTHER INFORMATION: peptide binding to TS

<400> SEQUENCE: 124

Gln Ser Phe
1

<210> SEQ ID NO 125
<211> LENGTH: 3
<212> TYPE: PRT
<213> ORGANISM: Artificial
<220> FEATURE:
<223> OTHER INFORMATION: peptide binding to TS

<400> SEQUENCE: 125

Asp Pro Leu
1

<210> SEQ ID NO 126
<211> LENGTH: 6
<212> TYPE: PRT
<213> ORGANISM: Artificial
<220> FEATURE:
<223> OTHER INFORMATION: peptide binding to TS

<400> SEQUENCE: 126

Ser Val Phe Gly Met Gln
1               5

<210> SEQ ID NO 127
<211> LENGTH: 6
<212> TYPE: PRT
<213> ORGANISM: Artificial
<220> FEATURE:
<223> OTHER INFORMATION: peptide binding to TS

<400> SEQUENCE: 127

Ser His Lys Pro Tyr Val
1               5

<210> SEQ ID NO 128
<211> LENGTH: 6
<212> TYPE: PRT
```

```
<213> ORGANISM: Artificial
<220> FEATURE:
<223> OTHER INFORMATION: peptide binding to TS

<400> SEQUENCE: 128

Arg Tyr Glu Ala His Leu
1               5

<210> SEQ ID NO 129
<211> LENGTH: 6
<212> TYPE: PRT
<213> ORGANISM: Artificial
<220> FEATURE:
<223> OTHER INFORMATION: peptide binding to TS

<400> SEQUENCE: 129

Trp Asn Pro Arg Asp Leu
1               5

<210> SEQ ID NO 130
<211> LENGTH: 6
<212> TYPE: PRT
<213> ORGANISM: Artificial
<220> FEATURE:
<223> OTHER INFORMATION: peptide binding to TS

<400> SEQUENCE: 130

Thr Leu Gly Ser Leu Glu
1               5

<210> SEQ ID NO 131
<211> LENGTH: 6
<212> TYPE: PRT
<213> ORGANISM: Artificial
<220> FEATURE:
<223> OTHER INFORMATION: peptide binding to TS

<400> SEQUENCE: 131

Pro Ile Trp Ser Ile Lys
1               5

<210> SEQ ID NO 132
<211> LENGTH: 8
<212> TYPE: PRT
<213> ORGANISM: Artificial
<220> FEATURE:
<223> OTHER INFORMATION: peptide binding to TS

<400> SEQUENCE: 132

Asp Asp Arg Arg Ile Ile Met Cys
1               5

<210> SEQ ID NO 133
<211> LENGTH: 8
<212> TYPE: PRT
<213> ORGANISM: Artificial
<220> FEATURE:
<223> OTHER INFORMATION: peptide binding to TS

<400> SEQUENCE: 133

Asp Asp Arg Arg Ile Ile Met Ser
1               5

<210> SEQ ID NO 134
<211> LENGTH: 8
<212> TYPE: PRT
<213> ORGANISM: Artificial
```

```
<220> FEATURE:
<223> OTHER INFORMATION: peptide binding to TS

<400> SEQUENCE: 134

Leu Leu Ser Ser Tyr Tyr Tyr Thr
1               5

<210> SEQ ID NO 135
<211> LENGTH: 8
<212> TYPE: PRT
<213> ORGANISM: Artificial
<220> FEATURE:
<223> OTHER INFORMATION: peptide binding to TS

<400> SEQUENCE: 135

Val Val Ser Ser Asp Asp His Ala
1               5

<210> SEQ ID NO 136
<211> LENGTH: 8
<212> TYPE: PRT
<213> ORGANISM: Artificial
<220> FEATURE:
<223> OTHER INFORMATION: peptide binding to TS

<400> SEQUENCE: 136

Arg Asp Trp Arg Lys Gly Lys His
1               5

<210> SEQ ID NO 137
<211> LENGTH: 8
<212> TYPE: PRT
<213> ORGANISM: Artificial
<220> FEATURE:
<223> OTHER INFORMATION: peptide binding to TS

<400> SEQUENCE: 137

Ile Ile Cys Trp Cys Cys Gly Val
1               5

<210> SEQ ID NO 138
<211> LENGTH: 8
<212> TYPE: PRT
<213> ORGANISM: Artificial
<220> FEATURE:
<223> OTHER INFORMATION: peptide binding to TS

<400> SEQUENCE: 138

Asn Trp Gly Gly Cys Ile Lys Arg
1               5

<210> SEQ ID NO 139
<211> LENGTH: 8
<212> TYPE: PRT
<213> ORGANISM: Artificial
<220> FEATURE:
<223> OTHER INFORMATION: peptide binding to TS

<400> SEQUENCE: 139

Arg Gly Cys Arg Thr Cys Val Cys
1               5

<210> SEQ ID NO 140
<211> LENGTH: 8
<212> TYPE: PRT
<213> ORGANISM: Artificial
<220> FEATURE:
```

<223> OTHER INFORMATION: peptide binding to TS

<400> SEQUENCE: 140

Cys Trp Gly Met Asp Cys Arg Asp
1               5

<210> SEQ ID NO 141
<211> LENGTH: 8
<212> TYPE: PRT
<213> ORGANISM: Artificial
<220> FEATURE:
<223> OTHER INFORMATION: peptide binding to TS

<400> SEQUENCE: 141

Cys Arg Lys Arg Ile Asp Trp Trp
1               5

<210> SEQ ID NO 142
<211> LENGTH: 8
<212> TYPE: PRT
<213> ORGANISM: Artificial
<220> FEATURE:
<223> OTHER INFORMATION: peptide binding to TS

<400> SEQUENCE: 142

Cys Cys Arg Gly Gly Phe Ile Ile
1               5

<210> SEQ ID NO 143
<211> LENGTH: 8
<212> TYPE: PRT
<213> ORGANISM: Artificial
<220> FEATURE:
<223> OTHER INFORMATION: peptide binding to TS

<400> SEQUENCE: 143

Asp Cys Asp Cys Ile Gly Glu Trp
1               5

<210> SEQ ID NO 144
<211> LENGTH: 8
<212> TYPE: PRT
<213> ORGANISM: Artificial
<220> FEATURE:
<223> OTHER INFORMATION: peptide binding to TS

<400> SEQUENCE: 144

Trp Arg Asp Ile Tyr Gly Cys Trp
1               5

<210> SEQ ID NO 145
<211> LENGTH: 8
<212> TYPE: PRT
<213> ORGANISM: Artificial
<220> FEATURE:
<223> OTHER INFORMATION: peptide binding to TS

<400> SEQUENCE: 145

Arg Ile Arg Arg Trp Arg Arg Ile
1               5

<210> SEQ ID NO 146
<211> LENGTH: 8
<212> TYPE: PRT
<213> ORGANISM: Artificial
<220> FEATURE:
<223> OTHER INFORMATION: peptide binding to TS

<400> SEQUENCE: 146

Gly Asp Lys Lys Gly Asp Arg Val
1               5

<210> SEQ ID NO 147
<211> LENGTH: 8
<212> TYPE: PRT
<213> ORGANISM: Artificial
<220> FEATURE:
<223> OTHER INFORMATION: peptide binding to TS

<400> SEQUENCE: 147

Leu Arg Lys Cys Arg Arg Asp Asp
1               5

<210> SEQ ID NO 148
<211> LENGTH: 8
<212> TYPE: PRT
<213> ORGANISM: Artificial
<220> FEATURE:
<223> OTHER INFORMATION: peptide binding to TS

<400> SEQUENCE: 148

Arg Ile Gly Arg Gly Ile Cys Arg
1               5

<210> SEQ ID NO 149
<211> LENGTH: 8
<212> TYPE: PRT
<213> ORGANISM: Artificial
<220> FEATURE:
<223> OTHER INFORMATION: peptide binding to TS

<400> SEQUENCE: 149

Gly Gly Gly Gly Lys Ile Leu Trp
1               5

<210> SEQ ID NO 150
<211> LENGTH: 8
<212> TYPE: PRT
<213> ORGANISM: Artificial
<220> FEATURE:
<223> OTHER INFORMATION: peptide binding to TS

<400> SEQUENCE: 150

Gly Cys Asp Trp Gly Lys His Arg
1               5

<210> SEQ ID NO 151
<211> LENGTH: 8
<212> TYPE: PRT
<213> ORGANISM: Artificial
<220> FEATURE:
<223> OTHER INFORMATION: peptide binding to TS

<400> SEQUENCE: 151

Glu Trp Lys Glu Arg Trp Gly Trp
1               5

<210> SEQ ID NO 152
<211> LENGTH: 8
<212> TYPE: PRT
<213> ORGANISM: Artificial
<220> FEATURE:
<223> OTHER INFORMATION: peptide binding to TS

```
<400> SEQUENCE: 152

Ile Trp Ile Gly Trp Asp Gly Trp
1               5

<210> SEQ ID NO 153
<211> LENGTH: 8
<212> TYPE: PRT
<213> ORGANISM: Artificial
<220> FEATURE:
<223> OTHER INFORMATION: peptide binding to TS

<400> SEQUENCE: 153

Trp Ile Arg Asp Gly Val Gly Gly
1               5

<210> SEQ ID NO 154
<211> LENGTH: 8
<212> TYPE: PRT
<213> ORGANISM: Artificial
<220> FEATURE:
<223> OTHER INFORMATION: peptide binding to TS

<400> SEQUENCE: 154

Arg Gly Lys Cys Trp Cys Cys Arg
1               5

<210> SEQ ID NO 155
<211> LENGTH: 8
<212> TYPE: PRT
<213> ORGANISM: Artificial
<220> FEATURE:
<223> OTHER INFORMATION: peptide binding to TS

<400> SEQUENCE: 155

Arg Asp Trp Cys Cys Phe Gly Arg
1               5

<210> SEQ ID NO 156
<211> LENGTH: 8
<212> TYPE: PRT
<213> ORGANISM: Artificial
<220> FEATURE:
<223> OTHER INFORMATION: peptide binding to TS

<400> SEQUENCE: 156

Cys Lys Cys Asp Met Trp Lys Trp
1               5

<210> SEQ ID NO 157
<211> LENGTH: 8
<212> TYPE: PRT
<213> ORGANISM: Artificial
<220> FEATURE:
<223> OTHER INFORMATION: peptide binding to TS

<400> SEQUENCE: 157

Arg Asp Gly Val Trp Arg Cys Glu
1               5

<210> SEQ ID NO 158
<211> LENGTH: 8
<212> TYPE: PRT
<213> ORGANISM: Artificial
<220> FEATURE:
<223> OTHER INFORMATION: peptide binding to TS

<400> SEQUENCE: 158
```

```
Trp Asp Ile Arg Asp Trp Phe Trp
1               5
```

<210> SEQ ID NO 159
<211> LENGTH: 8
<212> TYPE: PRT
<213> ORGANISM: Artificial
<220> FEATURE:
<223> OTHER INFORMATION: peptide binding to TS

<400> SEQUENCE: 159

```
Cys Cys Cys Cys Arg Trp Trp Ala
1               5
```

<210> SEQ ID NO 160
<211> LENGTH: 8
<212> TYPE: PRT
<213> ORGANISM: Artificial
<220> FEATURE:
<223> OTHER INFORMATION: peptide binding to TS

<400> SEQUENCE: 160

```
Gly Trp Lys Trp Cys Ile Trp Cys
1               5
```

<210> SEQ ID NO 161
<211> LENGTH: 8
<212> TYPE: PRT
<213> ORGANISM: Artificial
<220> FEATURE:
<223> OTHER INFORMATION: peptide binding to TS

<400> SEQUENCE: 161

```
Gly Arg Val Ile Ile Cys Gly Lys
1               5
```

<210> SEQ ID NO 162
<211> LENGTH: 8
<212> TYPE: PRT
<213> ORGANISM: Artificial
<220> FEATURE:
<223> OTHER INFORMATION: peptide binding to TS

<400> SEQUENCE: 162

```
Phe His Gly Asp Arg His Ile Arg
1               5
```

<210> SEQ ID NO 163
<211> LENGTH: 8
<212> TYPE: PRT
<213> ORGANISM: Artificial
<220> FEATURE:
<223> OTHER INFORMATION: peptide binding to TS

<400> SEQUENCE: 163

```
Cys Glu Arg Arg Asp Ile Asp Lys
1               5
```

<210> SEQ ID NO 164
<211> LENGTH: 8
<212> TYPE: PRT
<213> ORGANISM: Artificial
<220> FEATURE:
<223> OTHER INFORMATION: peptide binding to TS

<400> SEQUENCE: 164

```
Gly Val Ile Leu Arg Ile Asp Cys
1               5

<210> SEQ ID NO 165
<211> LENGTH: 8
<212> TYPE: PRT
<213> ORGANISM: Artificial
<220> FEATURE:
<223> OTHER INFORMATION: peptide binding to TS

<400> SEQUENCE: 165

His Trp Trp Trp Gly Phe Cys Trp
1               5

<210> SEQ ID NO 166
<211> LENGTH: 8
<212> TYPE: PRT
<213> ORGANISM: Artificial
<220> FEATURE:
<223> OTHER INFORMATION: peptide binding to TS

<400> SEQUENCE: 166

Asn Val Trp Val Arg Arg Ile Arg
1               5

<210> SEQ ID NO 167
<211> LENGTH: 8
<212> TYPE: PRT
<213> ORGANISM: Artificial
<220> FEATURE:
<223> OTHER INFORMATION: peptide binding to TS

<400> SEQUENCE: 167

Cys Gly Arg Trp Pro Gly Gly Cys
1               5

<210> SEQ ID NO 168
<211> LENGTH: 8
<212> TYPE: PRT
<213> ORGANISM: Artificial
<220> FEATURE:
<223> OTHER INFORMATION: peptide binding to TS

<400> SEQUENCE: 168

Trp Cys Arg Trp Trp Phe Trp Gly
1               5

<210> SEQ ID NO 169
<211> LENGTH: 8
<212> TYPE: PRT
<213> ORGANISM: Artificial
<220> FEATURE:
<223> OTHER INFORMATION: peptide binding to TS

<400> SEQUENCE: 169

Ile Lys Ile Leu Gly Trp Asp Trp
1               5

<210> SEQ ID NO 170
<211> LENGTH: 8
<212> TYPE: PRT
<213> ORGANISM: Artificial
<220> FEATURE:
<223> OTHER INFORMATION: peptide binding to TS
```

```
<400> SEQUENCE: 170

Trp Gly Trp Gly Ile Leu Lys Arg
1               5

<210> SEQ ID NO 171
<211> LENGTH: 8
<212> TYPE: PRT
<213> ORGANISM: Artificial
<220> FEATURE:
<223> OTHER INFORMATION: peptide binding to TS

<400> SEQUENCE: 171

Trp Cys Val Trp Ile Arg Arg Tyr
1               5

<210> SEQ ID NO 172
<211> LENGTH: 8
<212> TYPE: PRT
<213> ORGANISM: Artificial
<220> FEATURE:
<223> OTHER INFORMATION: peptide binding to TS

<400> SEQUENCE: 172

Asp Gly Gly Trp Cys Arg Gly Ile
1               5

<210> SEQ ID NO 173
<211> LENGTH: 8
<212> TYPE: PRT
<213> ORGANISM: Artificial
<220> FEATURE:
<223> OTHER INFORMATION: peptide binding to TS

<400> SEQUENCE: 173

Trp Gly Arg Ile Asn Trp Arg Phe
1               5

<210> SEQ ID NO 174
<211> LENGTH: 8
<212> TYPE: PRT
<213> ORGANISM: Artificial
<220> FEATURE:
<223> OTHER INFORMATION: peptide binding to TS

<400> SEQUENCE: 174

Arg Arg Met Cys Trp Leu Arg Gly
1               5

<210> SEQ ID NO 175
<211> LENGTH: 8
<212> TYPE: PRT
<213> ORGANISM: Artificial
<220> FEATURE:
<223> OTHER INFORMATION: peptide binding to TS

<400> SEQUENCE: 175

Arg Arg Gly Trp Val Ile Ile Pro
1               5

<210> SEQ ID NO 176
<211> LENGTH: 8
<212> TYPE: PRT
<213> ORGANISM: Artificial
<220> FEATURE:
<223> OTHER INFORMATION: peptide binding to TS
```

```
<400> SEQUENCE: 176

Gly Gly Phe Asp Val Asp Asp Asp
1               5

<210> SEQ ID NO 177
<211> LENGTH: 8
<212> TYPE: PRT
<213> ORGANISM: Artificial
<220> FEATURE:
<223> OTHER INFORMATION: peptide binidng to TS

<400> SEQUENCE: 177

Ile Pro Cys Lys Trp Arg Gly Cys
1               5

<210> SEQ ID NO 178
<211> LENGTH: 8
<212> TYPE: PRT
<213> ORGANISM: Artificial
<220> FEATURE:
<223> OTHER INFORMATION: peptide binding to TS

<400> SEQUENCE: 178

Ile Leu Asp Arg Cys Arg Trp Asp
1               5

<210> SEQ ID NO 179
<211> LENGTH: 8
<212> TYPE: PRT
<213> ORGANISM: Artificial
<220> FEATURE:
<223> OTHER INFORMATION: peptide binding to TS

<400> SEQUENCE: 179

Trp Cys Arg Gly Gly Cys Phe Cys
1               5

<210> SEQ ID NO 180
<211> LENGTH: 8
<212> TYPE: PRT
<213> ORGANISM: Artificial
<220> FEATURE:
<223> OTHER INFORMATION: peptide binding to TS

<400> SEQUENCE: 180

Cys Arg Asp Lys Val Trp Gly Gly
1               5

<210> SEQ ID NO 181
<211> LENGTH: 8
<212> TYPE: PRT
<213> ORGANISM: Artificial
<220> FEATURE:
<223> OTHER INFORMATION: peptide binding to TS

<400> SEQUENCE: 181

Gly Ile Lys Arg Trp Phe Ile Arg
1               5

<210> SEQ ID NO 182
<211> LENGTH: 8
<212> TYPE: PRT
<213> ORGANISM: Artificial
<220> FEATURE:
<223> OTHER INFORMATION: peptide binding to TS

<400> SEQUENCE: 182
```

```
Ile Cys Val Arg Ile Val Cys Ile
1               5
```

<210> SEQ ID NO 183
<211> LENGTH: 8
<212> TYPE: PRT
<213> ORGANISM: Artificial
<220> FEATURE:
<223> OTHER INFORMATION: peptide binding to TS

<400> SEQUENCE: 183

```
Cys Phe Ile Phe Ile Gly Trp Leu
1               5
```

<210> SEQ ID NO 184
<211> LENGTH: 8
<212> TYPE: PRT
<213> ORGANISM: Artificial
<220> FEATURE:
<223> OTHER INFORMATION: peptide binidng to TS

<400> SEQUENCE: 184

```
Ile Lys Trp Cys Gly Gly Val Lys
1               5
```

<210> SEQ ID NO 185
<211> LENGTH: 8
<212> TYPE: PRT
<213> ORGANISM: Artificial
<220> FEATURE:
<223> OTHER INFORMATION: peptide binding to TS

<400> SEQUENCE: 185

```
Cys Asp Cys Ile Arg Gly Gly Arg
1               5
```

<210> SEQ ID NO 186
<211> LENGTH: 325
<212> TYPE: PRT
<213> ORGANISM: Artificial
<220> FEATURE:
<223> OTHER INFORMATION: peptide binding to TS

<400> SEQUENCE: 186

```
Met Arg Gly Ser His His His His His Gly Ser Met Pro Val Ala
1               5                   10                  15

Gly Ser Glu Leu Pro Arg Arg Pro Leu Pro Ala Ala Gln Glu Arg
                20                  25                  30

Asp Ala Glu Pro Arg Pro Pro His Gly Glu Leu Gln Tyr Leu Gly Gln
        35                  40                  45

Ile Gln His Ile Leu Arg Cys Gly Val Arg Lys Asp Asp Arg Thr Gly
    50                  55                  60

Thr Gly Thr Leu Ser Val Phe Gly Met Gln Ala Arg Tyr Ser Leu Arg
65                  70                  75                  80

Asp Glu Phe Pro Leu Leu Thr Thr Lys Arg Val Phe Trp Lys Gly Val
                85                  90                  95

Leu Glu Glu Leu Leu Trp Phe Ile Lys Gly Ser Thr Asn Ala Lys Glu
                100                 105                 110

Leu Ser Ser Lys Gly Val Lys Ile Trp Asp Ala Asn Gly Ser Arg Asp
            115                 120                 125

Phe Leu Asp Ser Leu Gly Phe Ser Thr Arg Glu Glu Gly Asp Leu Gly
        130                 135                 140
```

-continued

```
Pro Val Tyr Gly Phe Gln Trp Arg His Phe Gly Ala Glu Tyr Arg Asp
145                 150                 155                 160

Met Glu Ser Asp Tyr Ser Gly Gln Gly Val Asp Gln Leu Gln Arg Val
                165                 170                 175

Ile Asp Thr Ile Lys Thr Asn Pro Asp Asp Arg Arg Ile Ile Met Cys
            180                 185                 190

Ala Trp Asn Pro Arg Asp Leu Pro Leu Met Ala Leu Pro Pro Cys His
        195                 200                 205

Ala Leu Cys Gln Phe Tyr Val Val Asn Ser Glu Leu Ser Cys Gln Leu
        210             215                 220

Tyr Gln Arg Ser Gly Asp Met Gly Leu Gly Val Pro Phe Asn Ile Ala
225                 230                 235                 240

Ser Tyr Ala Leu Leu Thr Tyr Met Ile Ala His Ile Thr Gly Leu Lys
                245                 250                 255

Pro Gly Asp Phe Ile His Thr Leu Gly Asp Ala His Ile Tyr Leu Asn
            260                 265                 270

His Ile Glu Pro Leu Lys Ile Gln Leu Gln Arg Glu Pro Arg Pro Phe
        275                 280                 285

Pro Lys Leu Arg Ile Leu Arg Lys Val Glu Lys Ile Asp Asp Phe Lys
    290                 295                 300

Ala Glu Asp Phe Gln Ile Glu Gly Tyr Asn Pro His Pro Thr Ile Lys
305                 310                 315                 320

Met Glu Met Ala Val
                325
```